United States Patent
Watanabe et al.

(10) Patent No.: US 7,612,155 B2
(45) Date of Patent: *Nov. 3, 2009

(54) FILM FORMING COMPOSITION, INSULATING FILM FORMED BY USE OF THE COMPOSITION, AND ELECTRONIC DEVICE

(75) Inventors: Yasufumi Watanabe, Shizuoka (JP); Katsuyuki Watanabe, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/790,357

(22) Filed: Apr. 25, 2007

(65) Prior Publication Data

US 2007/0255003 A1    Nov. 1, 2007

(30) Foreign Application Priority Data

Apr. 26, 2006  (JP) ............................. 2006-122534
Apr. 26, 2006  (JP) ............................. 2006-122535

(51) Int. Cl.
*C08F 38/00*  (2006.01)
*C08F 36/20*  (2006.01)
*C07C 13/615*  (2006.01)
*C08F 4/80*  (2006.01)

(52) U.S. Cl. .................. 526/282; 526/285; 585/22; 585/352; 524/550; 524/554

(58) Field of Classification Search ................ 526/282, 526/285; 585/22, 352; 524/550, 554
See application file for complete search history.

(56) References Cited

U.S. PATENT DOCUMENTS 3,342,880 A * 9/1967 Reinhardt .................... 570/187
3,378,587 A * 4/1968 Reinhardt .................... 564/456
3,457,318 A * 7/1969 Capaldi et. al. ............. 585/317

FOREIGN PATENT DOCUMENTS

JP     2003-292878 A    10/2003

OTHER PUBLICATIONS

Ishizone et al, Anionic Polymerizations of 1-Adamantyl Methacrylate and 3-Methacryloyloxy-1,1'-biadamantane, Macromol. Chem. Phys. 2002, 203, 2375-2384.*
Kobayashi et al, Living Anionic Polymerizations of 4-(1-Adamantyl)styrene and 3-(4-Vinylphenyl)-1,1'-diadamantane, Macromolecules 2006, 39, 5979-5986 (Published on Web Aug. 03, 2006).*

* cited by examiner

*Primary Examiner*—Fred M Teskin
(74) *Attorney, Agent, or Firm*—Sughrue Mion, PLLC

(57) ABSTRACT

A film forming composition includes a polymer of a compound represented by formula (I):

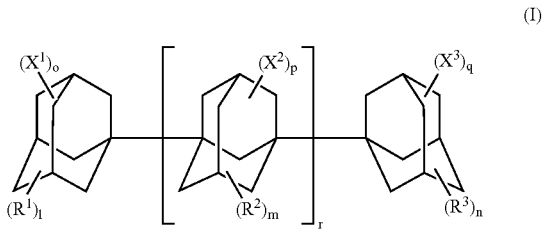

wherein $R^1$, $R^2$ and $R^3$ each independently represents a substituent containing a carbon-carbon double bond or carbon-carbon triple bond; $X^1$, $X^2$ and $X^3$ each independently represents any substituent; l and n each stands for an integer of from 0 to 15 and m stands for an integer of from 0 to 14, with the proviso that l, m and n do not represent 0 simultaneously; o and q each independently stands for an integer of from 0 to 15 and p independently stands for an integer of from 0 to 14; and r stands for 0 or 1, with the proviso that when r=0, $R^1$ and $R^3$ each independently represents a substituent containing a carbon-carbon double bond.

10 Claims, No Drawings

FILM FORMING COMPOSITION, INSULATING FILM FORMED BY USE OF THE COMPOSITION, AND ELECTRONIC DEVICE

BACKGROUND OF THE INVENTION

1. Field of the Invention

The present invention relates to a compound, polymer and film forming composition, more specifically, to an insulating film excellent in film properties such as dielectric constant and mechanical strength and usable for an electronic device and the like.

2. Background Art

In recent years, with the progress of high integration, multifunction and high performance in the field of electronic materials, circuit resistance and capacitance of a capacitor between interconnects have increased and have caused an increase in electric power consumption and delay time. Particularly, the increase in delay time becomes a large factor for reducing the signal speed of devices and generating crosstalk. Reduction of parasitic resistance and parasitic capacitance are therefore required in order to reduce this delay time, thereby attaining speed-up of devices. As one of the concrete measures for reducing this parasitic capacitance, an attempt has been made to cover the periphery of an interconnect with a low dielectric interlayer insulating film. The interlayer insulating film is expected to have superior heat resistance in the thin film formation step when a printed circuit board is manufactured or in post steps such as chip connection and pin attachment and also chemical resistance in the wet process. In addition, a low resistance Cu interconnect has been introduced in recent years instead of an Al interconnect, and with this tendency, CMP (chemical mechanical polishing) has been employed commonly for planarization of the film surface. Accordingly, an insulating film having high mechanical strength and capable of withstanding this CMP step is required.

As an insulating film having high heat resistance, a polybenzoxazole or polyimide film is widely known. Since it contains an N atom having high polarity, it is not satisfactory from the viewpoints of low dielectric properties, low water absorption, durability and hydrolysis resistance.

Furthermore, organic polymers as described above generally have insufficient solubility in an organic solvent and it becomes an important problem for them to prevent precipitation in the coating solvent or entrapment of particulates in an insulating film. When the polymer main chain is modified to have a folded structure so as to increase the solubility, this disadvantageously causes reduction in both the glass transition point and the heat resistance and it is not easy to satisfy both of these properties at the same time.

Also, a highly heat-resistant resin having a polyarylene ether as the basic main chain is known and it has a relative dielectric constant of from 2.6 to 2.7. In order to realize a high-speed device, however, reduction in the dielectric constant, more specifically, reduction in the relative dielectric constant to preferably 2.6 or less, more preferably 2.5 or less in the form of a bulk without porosification is desired.

An insulating film using a thermal polymer of adamantane substituted with an ethynyl group is disclosed in JP-A-2003-292878 (the term "JP-A" as used herein means an "unexamined published Japanese patent application"). However, since this monomer is polymerized without using a polymerization catalyst, it takes long hours to complete the reaction. This results in various problems, for example, an undesirable side reaction such as air oxidation proceeds and causes an increase in the relative dielectric constant of an insulating film thus obtained and by-production of a large amount of a polymer sparingly soluble in a coating solvent worsens the surface condition of the insulating film.

SUMMARY OF THE INVENTION

The invention relates to a film forming composition for overcoming the above-described problems. More specifically, the invention provides a film-forming composition uniform without precipitation of an insoluble matter and capable of forming a film with a good surface condition, and further provides a film-forming composition to be used in electronic devices, excellent in properties such as dielectric constant and mechanical strength and capable of forming an insulating film with a good surface condition, an insulating film formed using the composition and an electronic device having the insulating film. (An "insulating film" is also referred to as a "dielectric film" or a "dielectric insulating film", and these terms are not substantially distinguished.) The invention further pertains to a polymer contained in the film forming composition and a compound used for the synthesis of the polymer.

It has been found that the problems can be overcome by the below-described constitutions <1> to <17>.

<1> A film forming composition comprising a polymer of a compound represented by formula (I):

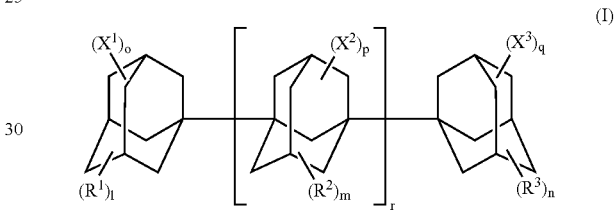

wherein $R^1$, $R^2$ and $R^3$ each independently represents a substituent containing a carbon-carbon double bond or carbon-carbon triple bond;

$X^1$, $X^2$ and $X^3$ each independently represents any substituent;

l and n each stands for an integer of from 0 to 15 and m stands for an integer of from 0 to 14, with the proviso that l, m and n do not represent 0 simultaneously;

o and q each independently stands for an integer of from 0 to 15 and p independently stands for an integer of from 0 to 14; and r stands for 0 or 1, with the proviso that when r=0, $R^1$ and $R^3$ each independently represents a substituent containing a carbon-carbon double bond.

<2> The film forming composition as described in <1>, wherein the polymer of the compound represented by formula (I) is obtained by polymerizing the compound represented by formula (I) in the presence of a polymerization accelerator.

<3> The film forming composition as described in <2>, wherein the polymerization accelerator is a transition metal catalyst.

<4> The film forming composition as described in <3>, wherein the transition metal catalyst is a palladium catalyst.

<5> The film forming composition as described in <2>, wherein the polymerization accelerator is a radical polymerization initiator.

<6> The film forming composition as described in <5>, wherein the radical polymerization initiator is selected from the group consisting of organic peroxides and azo compounds.

<7> The film forming composition as described in <1>,
wherein the polymer of the compound represented by formula (I) has a solubility of 1 mass % or greater in cyclohexanone at 25° C.

<8> The film forming composition as described in <2>,
wherein the polymerization accelerator is in an amount of from 0.001 to 2 moles per 1 mole of the compound represented by the formula (I).

<9> The film forming composition as described in <1>,
further comprising a coating solvent.

<10> The film forming composition as described in <1>,
further comprising a pore-forming agent.

<11> The film forming composition as described in <1>,
further comprising an adhesion accelerator.

<12> An insulating film formed by use of the film forming composition as described in <1>.

<13> An electronic device comprising the insulating film as described in <12>.

<14> A compound represented by formula (I):

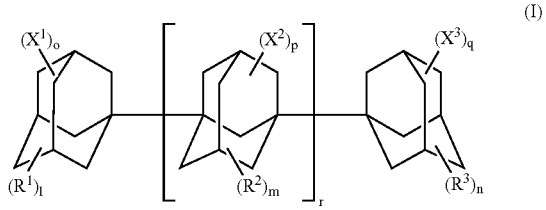

wherein $R^1$, $R^2$ and $R^3$ each independently represents a substituent containing a carbon-carbon double bond or carbon-carbon triple bond;

$X^1$, $X^2$ and $X^3$ each independently represents any substituent;

l and n each stands for an integer of from 0 to 15 and m stands for an integer of from 0 to 14, with the proviso that l, m and n do not represent 0 simultaneously;

o and q each independently stands for an integer of from 0 to 15 and p independently stands for an integer of from 0 to 14; and r stands for 0 or 1, with the proviso that when r=0, $R^1$ and $R^3$ each independently represents a substituent containing a carbon-carbon double bond.

<15> The compound represented by formula (I) as described in <14>,
wherein $R^1$, $R^2$ and $R^3$ each represents an ethynyl group, $X^1$, $X^2$ and $X^3$ each represents a hydrogen atom or a linear or branched $C_{1-10}$ alkyl group;

l and n each independently represents 0 or 1 with the proviso that l and n do not represent 0 simultaneously, m stands for 0; and o, p and q each independently stands for an integer of from 0 to 2.

<16> A polymer obtained by polymerizing a compound represented by formula (I):

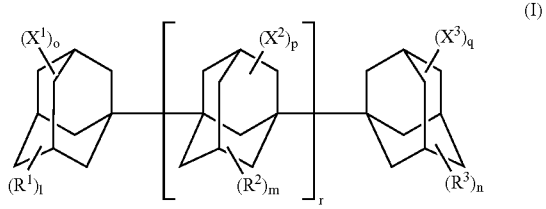

wherein $R^1$, $R^2$ and $R^3$ each independently represents a substituent containing a carbon-carbon double bond or carbon-carbon triple bond;

$X^1$, $X^2$ and $X^3$ each independently represents any substituent;

l and n each stands for an integer of from 0 to 15 and m stands for an integer of from 0 to 14, with the proviso that l, m and n do not represent 0 simultaneously;

o and q each independently stands for an integer of from 0 to 15 and p independently stands for an integer of from 0 to 14; and r stands for 0 or 1, with the proviso that when r=0, $R^1$ and $R^3$ each independently represents a substituent containing a carbon-carbon double bond.

<17> The polymer of the compound represented by formula (I) as described in <16>, which is obtained by polymerizing the compound represented by formula (I) in the presence of a polymerization accelerator.

DETAILED DESCRIPTION OF THE INVENTION

The invention will hereinafter be described specifically.

The polymer contained in the film forming composition of the invention is a polymer of a compound represented by the formula (I), preferably a polymer obtained by polymerizing the compound represented by the formula (I) in the presence of a polymerization accelerator.

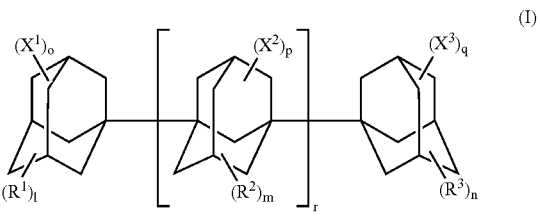

wherein:
$R^1$, $R^2$ and $R^3$ each independently represents a substituent containing a carbon-carbon double bond or carbon-carbon triple bond;

$X^1$, $X^2$ and $X^3$ each independently represents any substituent;

l and n each independently stands for an integer of from 0 to 15 and m independently stands for an integer of from 0 to 14, with the proviso that l, m and n do not represent 0 simultaneously;

o and q each independently stands for an integer of from 0 to 15 and p independently stands for an integer of from 0 to 14; and r stands for 0 or 1, with the proviso that when r=0, $R^1$ and $R^3$ each independently represents a substituent containing a carbon-carbon double bond.

The compound represented by formula (I) has at least one group containing a carbon-carbon double bond or a carbon-carbon triple bond as $R^1$, $R^2$ or $R^3$ which is a substituent to the bisadamantane or trisadamantane skeleton. When the skeleton is a bisadamantane, that is, when r=0, however, the compound has at least one group containing a carbon-carbon double bond as $R^1$ or $R^3$.

Preferred examples of the substituent containing a carbon-carbon double bond or carbon-carbon triple bond as $R^1$, $R^2$ or $R^3$ include alkenyl groups (preferably alkenyl groups having from 2 to 10 carbon atoms in total such as vinyl, allyl, 1-propenyl, 2-buten-1-yl and 1-buten-4-yl), alkynyl groups (preferably alkynyl groups having from 2 to 10 carbon atoms in total such as ethynyl, propargyl, 2-butyn-1-yl and 1-butyn-4-yl, and 1-hexin-6-yl), and aryl groups having a carbon-carbon double bond or carbon-carbon triple bond as a substituent (preferably aryl groups having from 8 to 30 carbon atoms in total such as 4-vinylphenyl, 3,5-divinylphenyl, 4-ethynylphenyl and 3,5-diethynylphenyl).

The substituent as $R^1$, $R^2$ or $R^3$ is preferably an alkenyl group or alkynyl group, more preferably an alkynyl group, especially preferably, an ethynyl group. When r=0, the substituent as $R^1$ or $R^3$ is preferably an alkenyl group, more preferably an alkenyl group having, at the end thereof, —CH=CH$_2$, especially preferably a vinyl group.

The group containing a carbon-carbon double bond or carbon-carbon triple bond may further has another substituent, and examples of the another substituent include halogen atoms (fluorine, chlorine, bromine and iodine), linear, branched or cyclic alkyl groups ($C_{1-20}$, preferably $C_{1-10}$ alkyl groups such as methyl, t-butyl, cyclopentyl, cyclohexyl, adamantyl, biadamantyl and diamantyl), alkynyl groups ($C_{2-10}$ alkynyl groups such as ethynyl and phenylethynyl), aryl groups ($C_{6-10}$ aryl groups such as phenyl, 1-naphthyl and 2-naphthyl), acyl groups ($C_{1-10}$ acyl groups such as acetyl and benzoyl), aryloxy groups ($C_{6-10}$ aryloxy groups such as phenoxy), arylsulfonyl groups ($C_{6-10}$ arylsulfonyl groups such as phenylsulfonyl), nitro group, cyano group, silyl groups ($C_{1-10}$ silyl groups such as triethoxysilyl, methyldiethoxysilyl and trivinylsilyl), alkoxycarbonyl groups ($C_{2-10}$ alkoxycarbonyl groups such as methoxycarbonyl) and carbamoyl groups ($C_{1-10}$ carbamoyl groups such as carbamoyl and N,N-dimethylcarbamoyl). These substituents each may be substituted further by another substituent.

The bisadamantane or trisadamantane skeleton in the compound represented by the formula (I) may have, as $X^1$, $X^2$ or $X^3$, any substituent. Examples of the any substituent include halogen atoms (fluorine, chlorine, bromine and iodine), alkyl groups ($C_{1-20}$, preferably $C_{1-10}$ alkyl groups such as methyl, t-butyl, cyclopentyl, cyclohexyl, adamantyl, biadamantyl and diamantyl), acyl groups ($C_{2-10}$ acyl groups such as acetyl and benzoyl), aryloxy groups ($C_{6-10}$ aryloxy groups such as phenoxy), arylsulfonyl groups ($C_{6-10}$ arysulfonyl groups such as phenylsulfonyl), nitro group, cyano group and silyl groups ($C_{1-10}$ silyl groups such as triethoxysilyl, methyldiethoxysilyl and trivinylsilyl). As the substituent, $C_{1-5}$ alkyl groups are preferred, of which methyl and ethyl groups are more preferred, with the methyl group being most preferred.

The number (l, m or n) of the substituent containing a carbon-carbon double bond or carbon-carbon triple bond per adamantane skeleton in the compound represented by the formula (I) is preferably from 0 to 4, more preferably from 0 to 2, especially preferably 0 or 1. The total number of the substituents represented by $R^1$, $R^2$ and $R^3$, that is, l+m+n is preferably from 1 to 6, more preferably from 1 to 4, especially preferably 2.

The total number of the substituents represented by $X^1$, $X^2$ and $X^3$, that is, o+p+q per adamantane skeleton in the formula (I) is preferably from 0 to 6, more preferably from 0 to 3, especially preferably from 0 to 2.

The molecular weight of the compound represented by formula (I) is preferably from 296 to 7,000, more preferably from 296 to 600, especially preferably from 296 to 400.

Examples of the polymer contained in the film forming composition of the invention include homopolymer of the compound represented by the formula (I), copolymers between the compound represented by the formula (I) and another polymerizable compound, copolymers of two or more of the compounds represented by the formula (I), and copolymers of two or more of the compounds represented by the formula (I) and another polymerizable compound.

Specific examples of the compound represented by the formula (I) will next be shown, but the compound is not limited thereto.

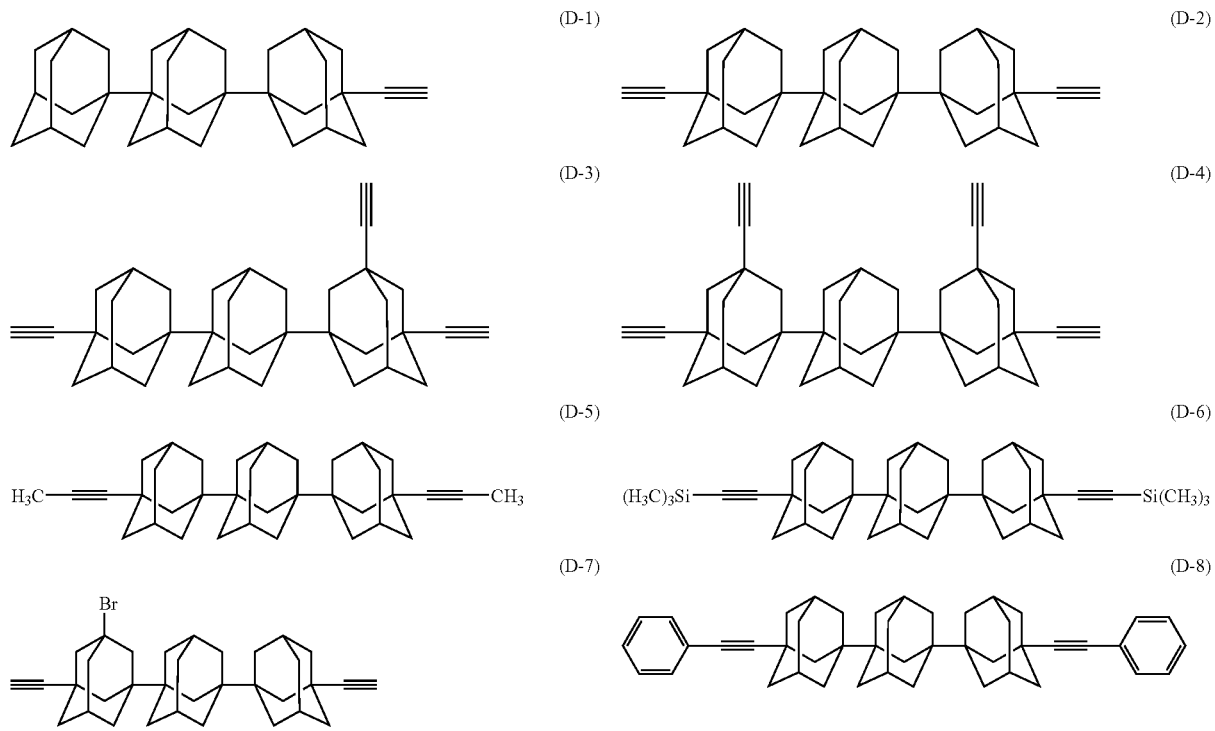

-continued
(D-9)
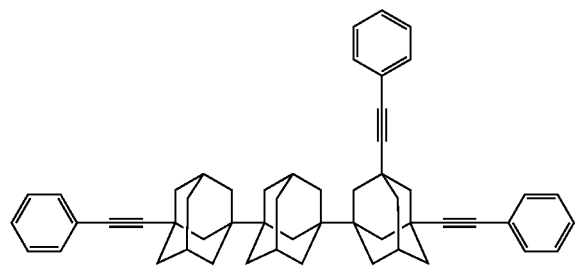
(D-10)
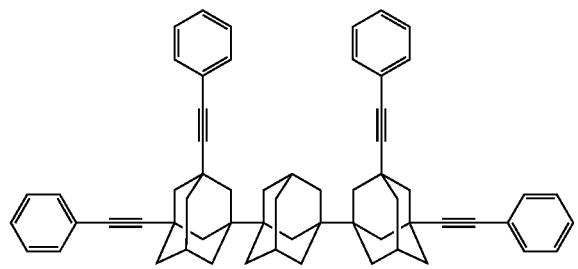
(D-11)
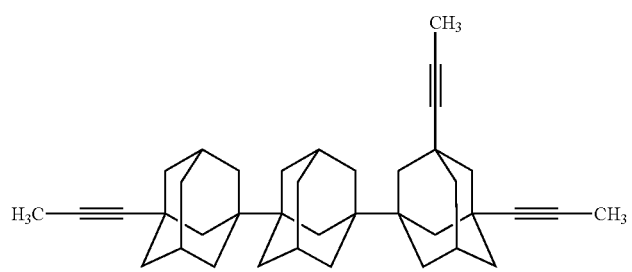
(D-12)
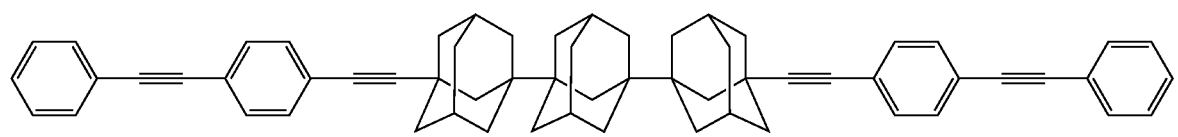
(D-13)
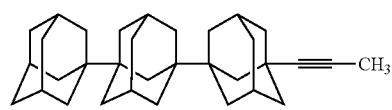
(D-14)
(D-15)
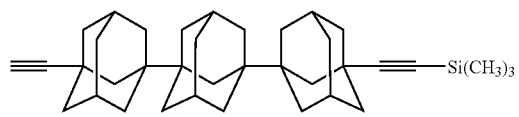
(D-16)
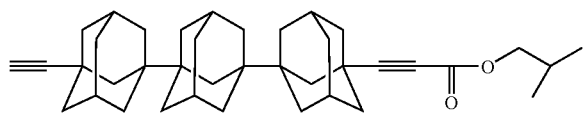
(D-17)
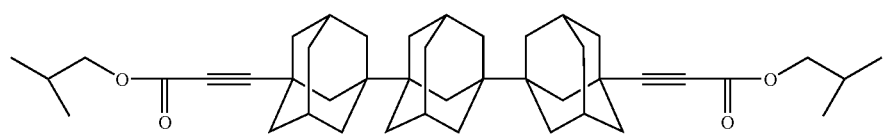
(D-18)
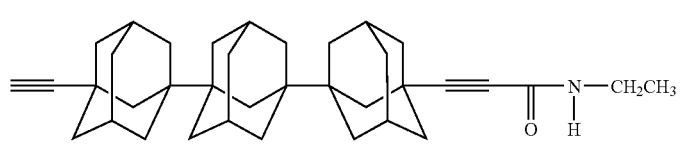

-continued
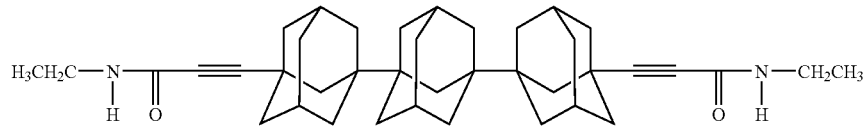
(D-19)
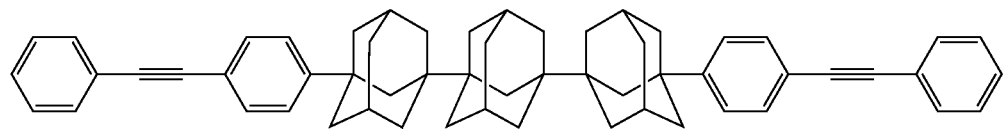
(D-20)
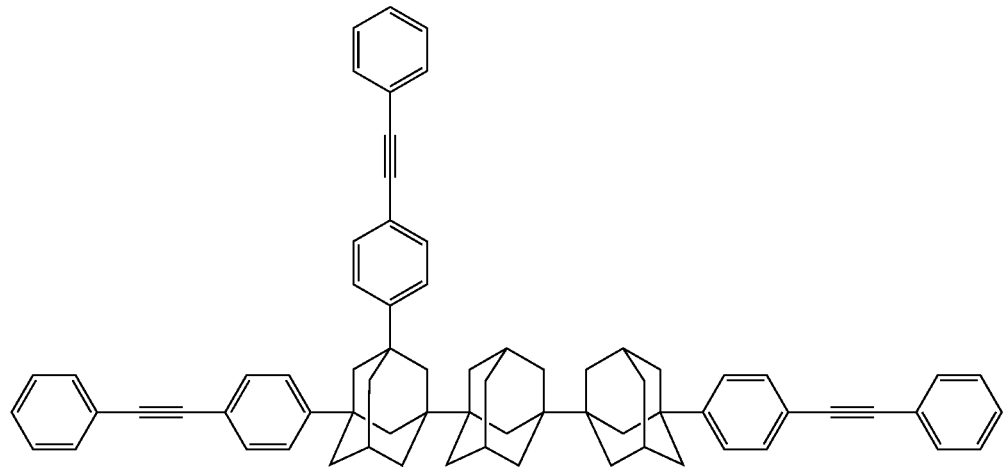
(D-21)
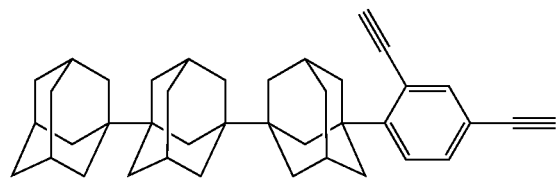
(D-22)
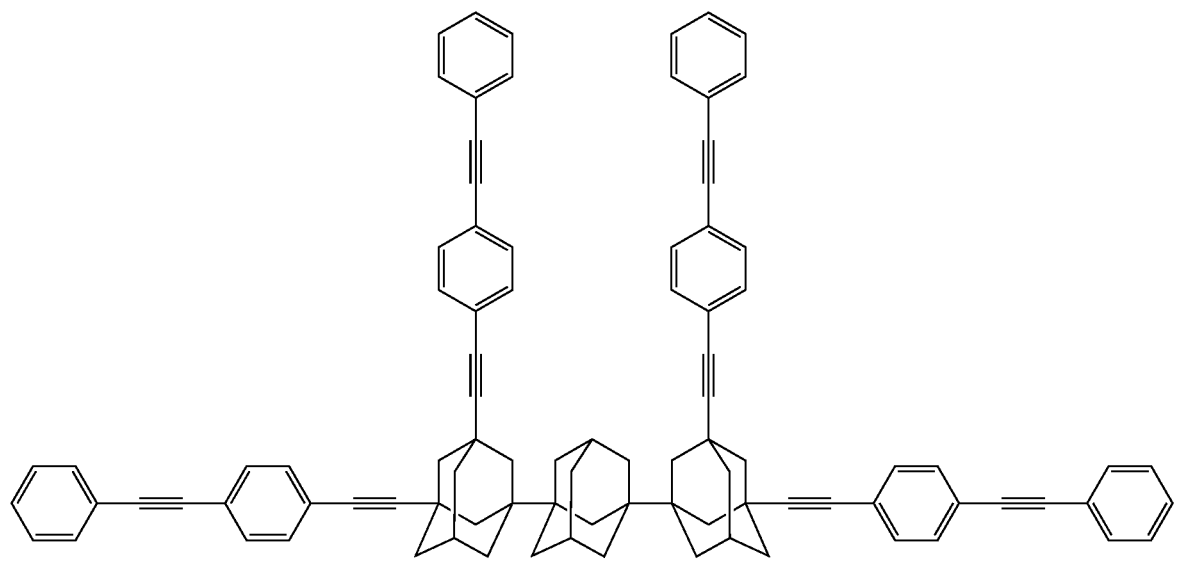
(D-23)

-continued
(D-24)
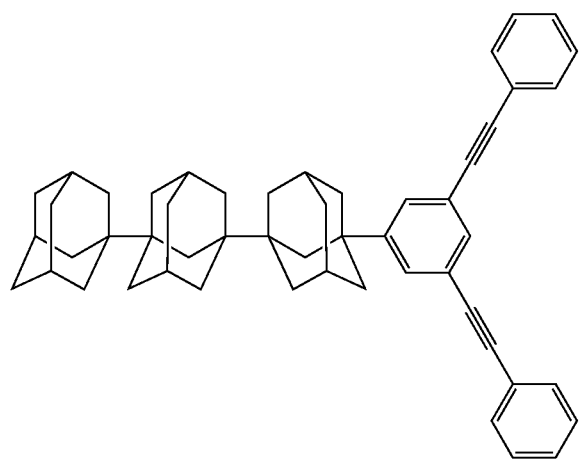
(D-25)
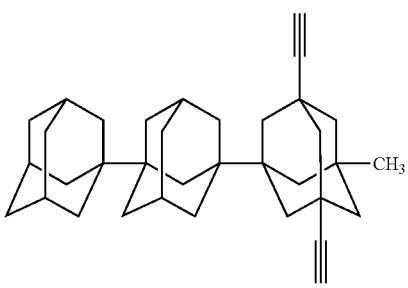
(D-26)
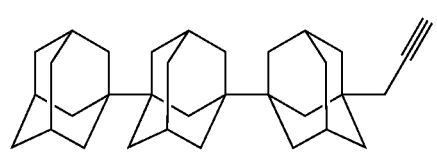
(D-27)
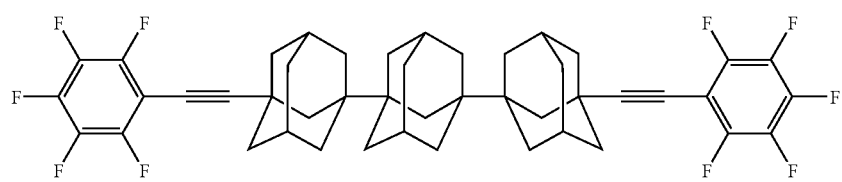
(D-28)
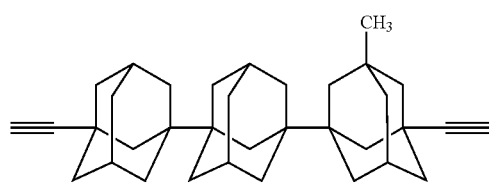
(D-29)
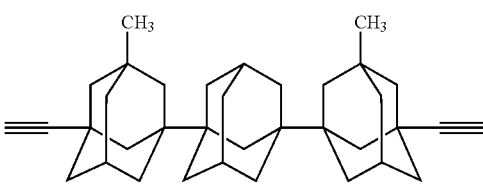
(D-30)
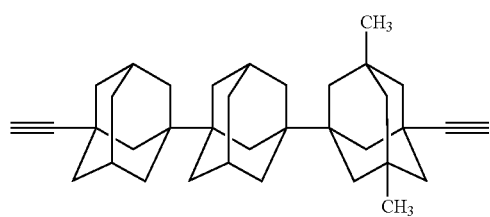
(D-31)
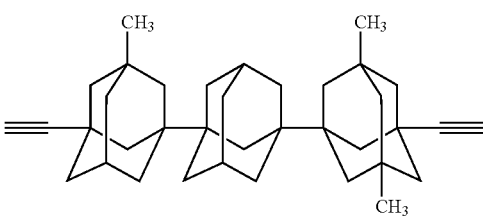
(D-32)
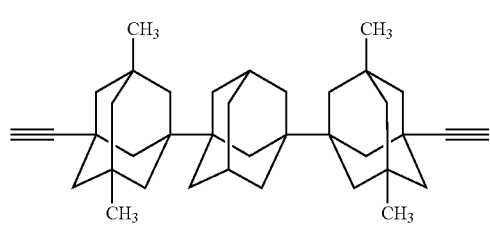
(D-33)
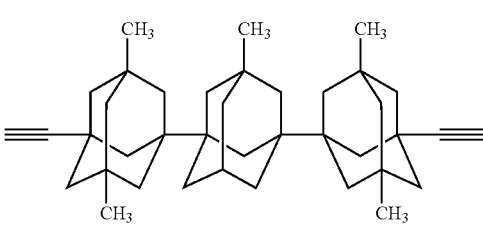

-continued
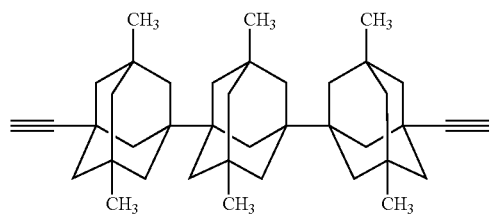
(D-34)
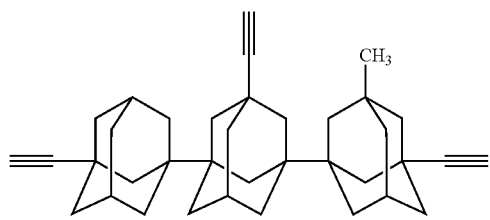
(D-35)
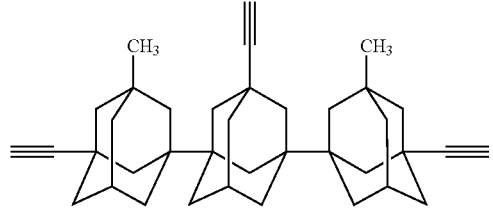
(D-36)
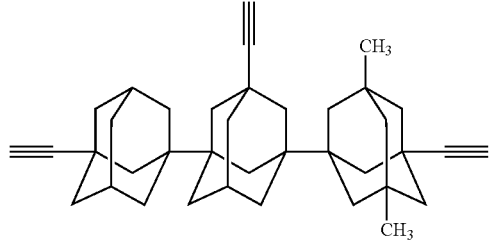
(D-37)
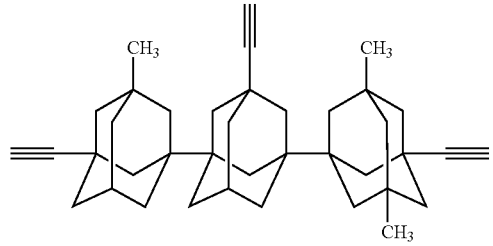
(D-38)
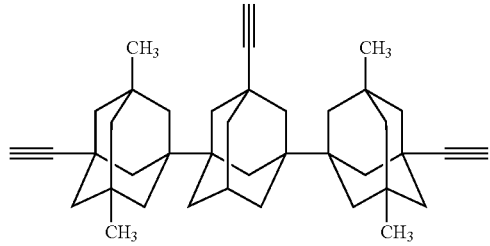
(D-39)
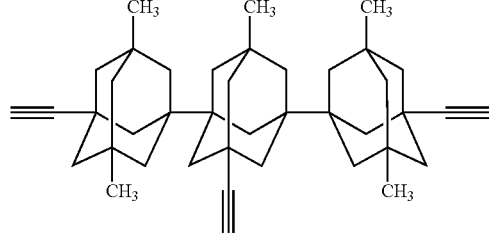
(D-40)
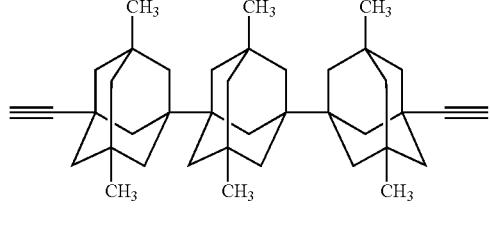
(D-41)
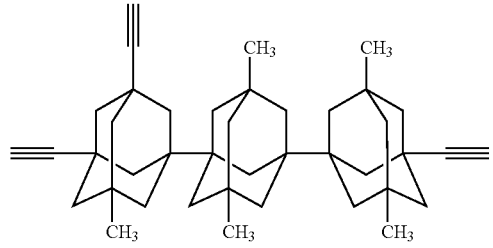
(D-42)
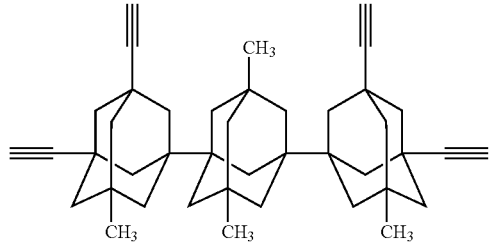
(D-43)
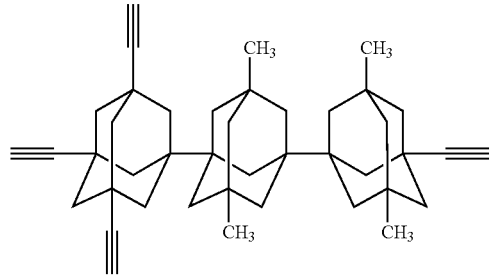
(D-44)
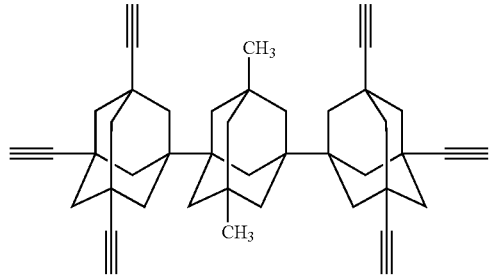
(D-45)

-continued
(D-101)
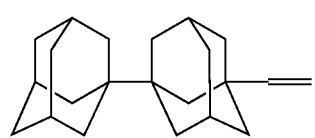
(D-102)
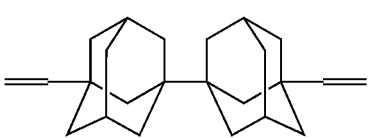
(D-103)
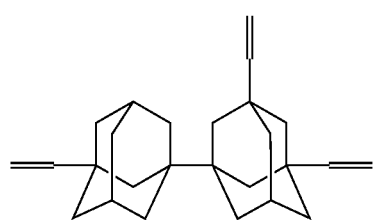
(D-104)
(D-105)
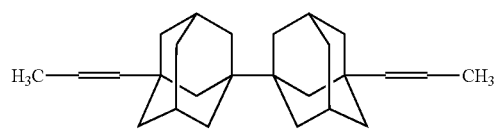
(D-106)
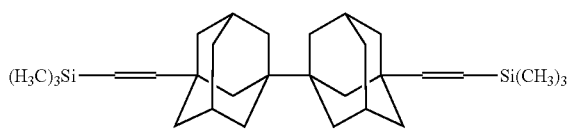
(D-107)
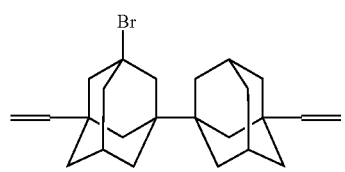
(D-108)
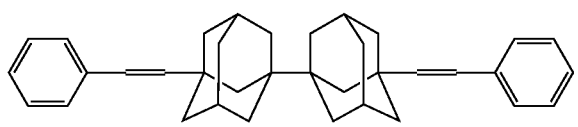
(D-109)
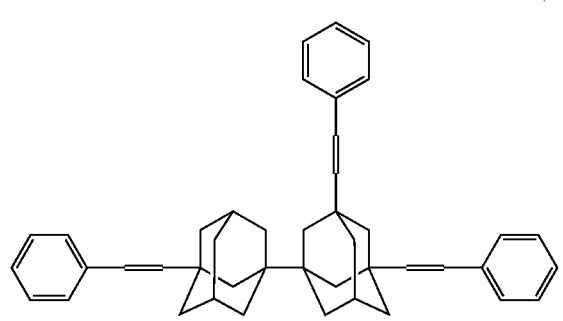
(D-110)
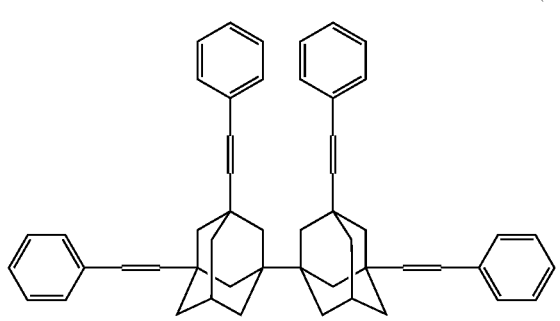
(D-111)
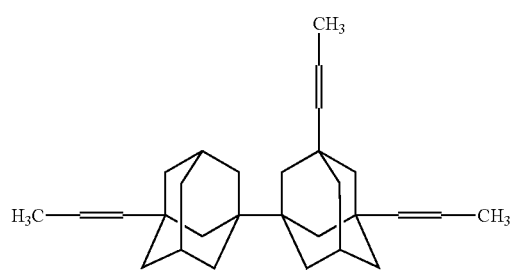

-continued
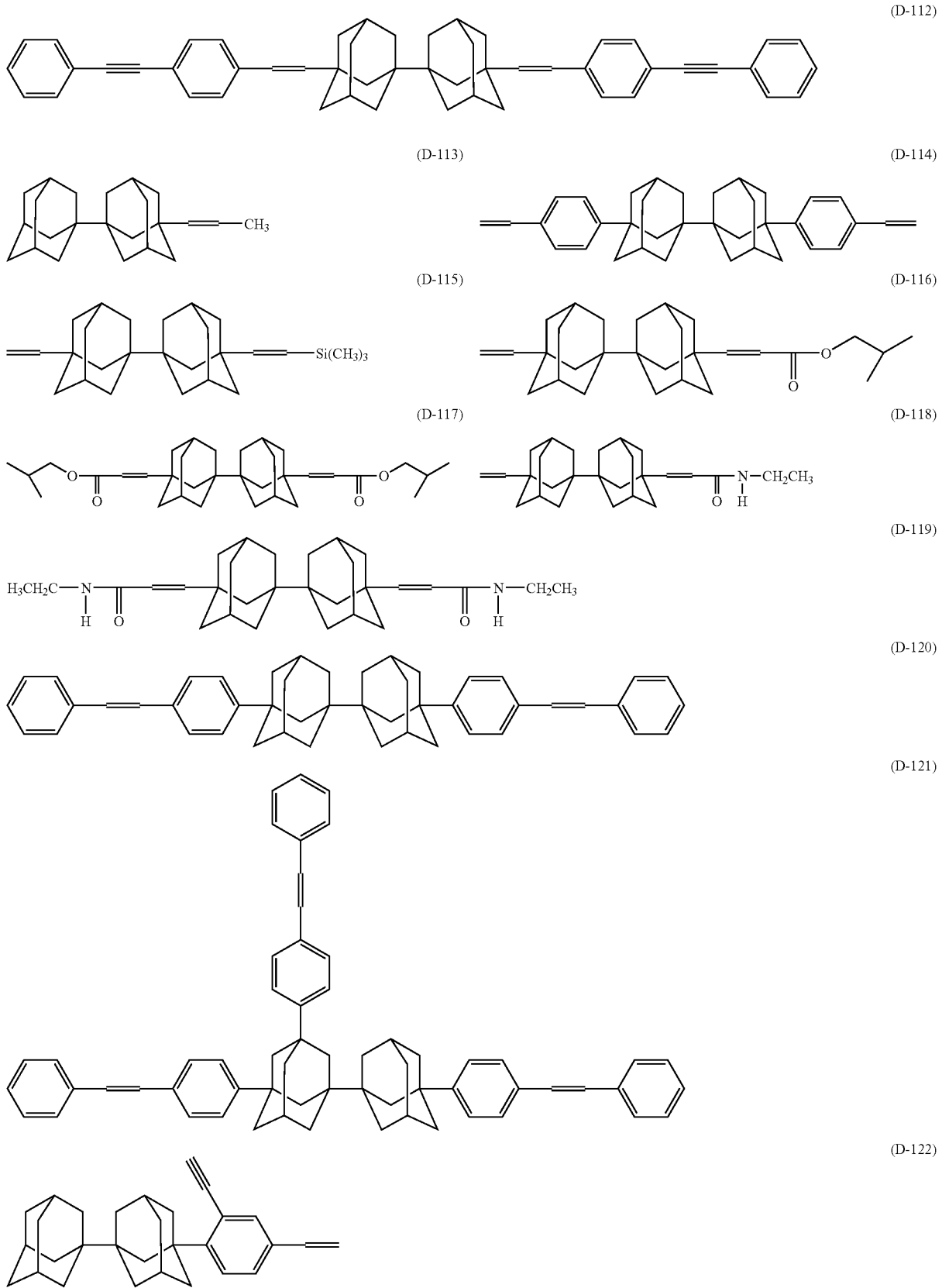

-continued
(D-123)
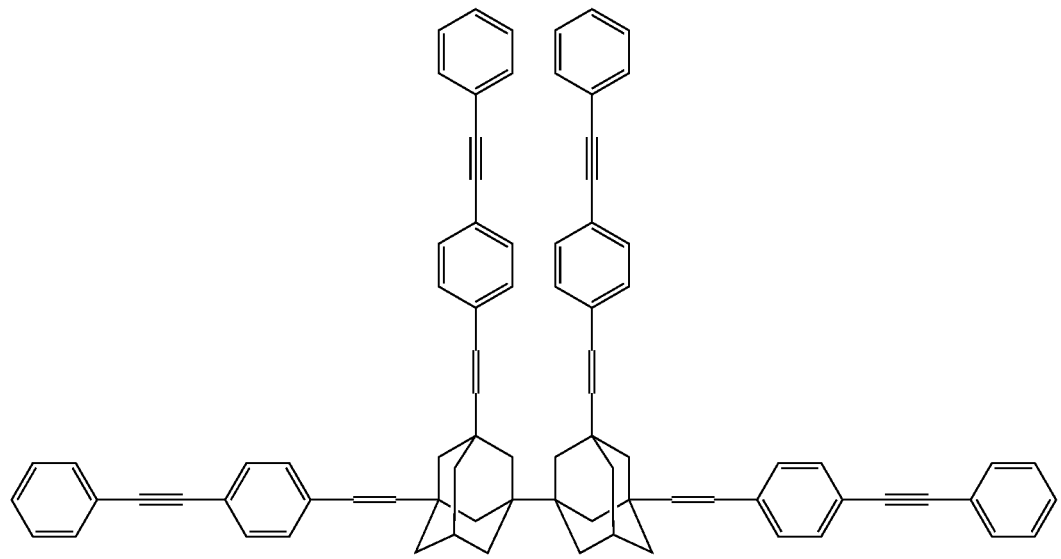
(D-124)
(D-125)
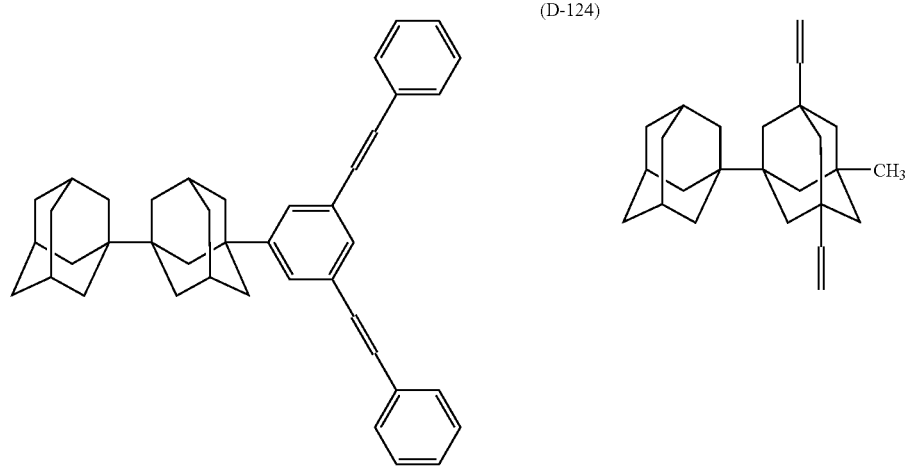
(D-126) (D-127)
(D-128) (D-129)
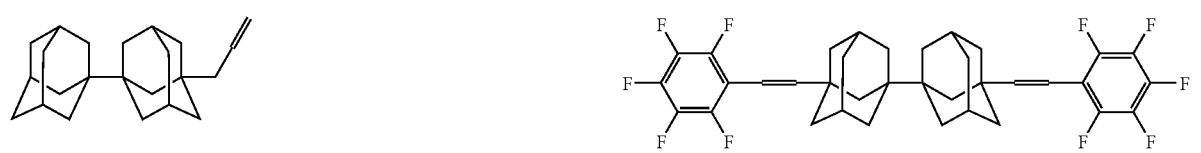
(D-130) (D-131)
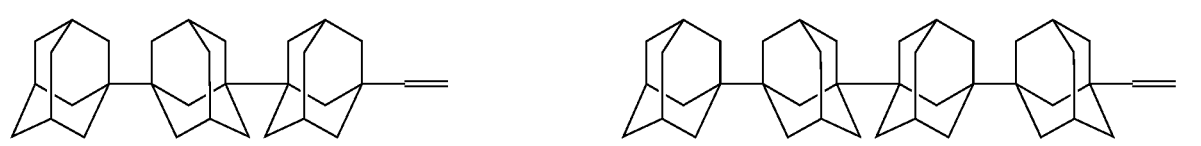
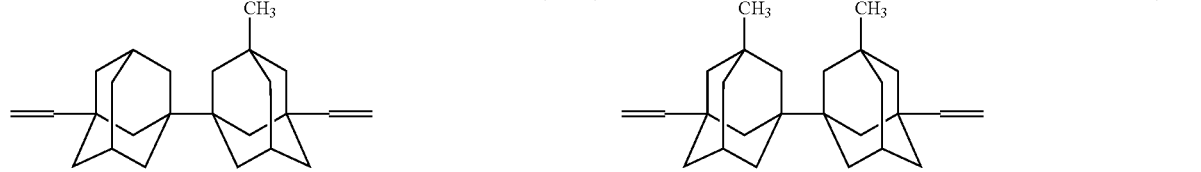

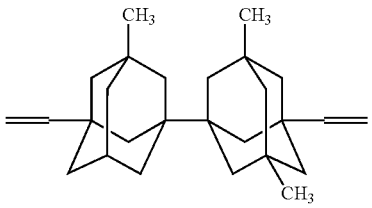

(D-133)

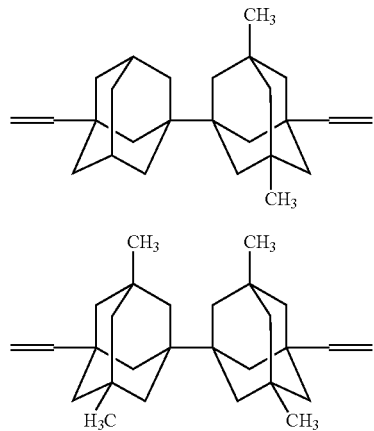

(D-132)

(D-134)

When the substituent having a carbon-carbon double bond is introduced into the bisadamantane or trisadamantane skeleton for the synthesis of the compound represented by formula (I), a known synthesis process can be employed. For example, a vinyl group can be introduced easily by using a commercially available bromine-substituted adamantane as a raw material to prepare bisadamantane or trisadamantane, brominating the resulting product into bromine-substituted bisadamantane or trisadamantane, causing a Friedel-Crafts reaction of it with vinyl bromide in the presence of a Lewis acid such as aluminum bromide, aluminum chloride or iron chloride to introduce a 2,2-dibromoethyl group, treating the resulting product with a strong base to eliminate HBr, and reducing the residue with diisobutylaluminum hydride (DIBAL-H) or the like. An aryl group can also be introduced easily by a Friedel-Crafts reaction of a bromine-substituted bisadamantane or trisadamantane with an aromatic compound.

For the introduction of the substituent containing a carbon-carbon triple bond into the trisadamantane skeleton in the synthesis of the compound represented by the formula (I), a known synthesis process can be employed. For example, an ethynyl group can be introduced easily by using commercially available bromine-substituted adamantane as a raw material to prepare trisadamantane, brominating the resulting product to prepare bromine-substituted trisadamantane, causing a Friedel-Crafts reaction of the product with vinyl bromine in the presence of a Lewis acid such as aluminum bromide, aluminum chloride or iron chloride to introduce a 2,2-dibromoethyl group, and then treating the resulting product with a strong base to eliminate HBr. An aryl group can also be introduced easily by a Friedel-Crafts reaction of a bromine-substituted trisadamantane with an aryl derivative.

The polymerization of the compound of the formula (I) is preferably performed in a solvent.

For the polymerization reaction of the compound (I), any solvent is usable insofar as it can dissolve therein a raw material monomer at a required concentration and does not adversely affect the properties of the film formed from the obtained polymer. Examples of the solvent usable for the polymerization include water; alcohol solvents such as methanol, ethanol and propanol; ketone solvents such as acetone, alcohol-acetone, methyl ethyl ketone, methyl isobutyl ketone, cyclohexanone and acetophenone; ester solvents such as ethyl acetate, butyl acetate, propylene glycol monomethyl ether acetate, γ-butyrolactone and methyl benzoate; ether solvents such as dibutyl ether, anisole and tetrahydrofuran; aromatic hydrocarbon solvents such as toluene, xylene, mesitylene, 1,2,4,5-tetramethylbenzene, pentamethylbenzene, isopropylbenzene, 1,4-diisopropylbenzene, t-butylbenzene, 1,4-di-t-butylbenzene, 1,3,5-triethylbenzene, 1,3,5-tri-t-butylbenzene, 4-t-butyl-orthoxylene, 1-methylnaphthalene and 1,3,5-triisopropylbenzene; amide solvents such as N-methylpyrrolidinone and dimethylacetamide; halogen solvents such as carbon tetrachloride, dichloromethane, chloroform, 1,2-dichloroethane, chlorobenzene, 1,2-dichlorobenzene and 1,2,4-trichlorobenzene; and aliphatic hydrocarbon solvents such as hexane, heptane, octane and cyclohexane.

Of these solvents, preferred are acetone, methyl ethyl ketone, methyl isobutyl ketone, cyclohexanone, acetophenone, ethyl acetate, propylene glycol monomethyl ether acetate, γ-butyrolactone, anisole, tetrahydrofuran, toluene, xylene, mesitylene, 1,2,4,5-tetramethylbenzene, isopropylbenzene, t-butylbenzene, 1,4-di-t-butylbenzene, 1,3,5-tri-t-butylbenzene, 4-t-butyl-orthoxylene, 1-methylnaphthalene, 1,3,5-triisopropylbenzene, 1,2-dichloroethane, chlorobenzene, 1,2-dichlorobenzene and 1,2,4-trichlorobenzene; more preferred are tetrahydrofuran, γ-butyrolactone, anisole, toluene, xylene, mesitylene, isopropylbenzene, t-butylbenzene, 1,3,5-tri-t-butylbenzene, 1-methylnaphthalene, 1,3,5-triisopropylbenzene, 1,2-dichloroethane, chlorobenzene, 1,2-dichlorobenzene and 1,2,4-trichlorobenzene; and especially preferred are γ-butyrolactone, anisole, mesitylene, t-butylbenzene, 1,3,5-triisopropylbenzene, 1,2-dichlorobenzene and 1,2,4-trichlorobenzene. These solvents may be used either singly or in combination.

The boiling point of the organic solvent to be used for the polymerization reaction is preferably 50° C. or greater, more preferably 100° C. or greater, especially preferably 150° C. or greater.

The concentration of the reaction solution is preferably from 1 to 50 mass %, more preferably from 5 to 30 mass %, especially preferably from 10 to 20 mass %.

The polymerization of the compound represented by formula (I) of the invention is preferably performed by an addition-polymerization reaction of a carbon-carbon double bond or carbon-carbon triple bond. As the addition-polymerization reaction in the invention, for example, cationic polymerization, anionic polymerization, radical polymerization and thermal polymerization, which are known in the field of organic synthesis, may be utilized.

In the invention, the polymerization reaction of the compound represented by formula (I) is performed preferably in the presence of a polymerization accelerator. Examples of the polymerization accelerator include metal catalysts and radical polymerization initiators.

Use of a metal catalyst has the merits such as reduction in the reaction time and reaction temperature. In the invention, in particular, it has an excellent effect in preparing a polymer having good solubility in a coating solvent in a high yield. The metal catalyst usable in the polymerization reaction is preferably a transition metal catalyst, and preferred examples include palladium catalysts such as $Pd(PPh_3)_4$, bis(benzonitrile)palladium chloride and $Pd(OAc)_2$; Ziegler-Natta catalysts; Ni catalysts such as nickel acetylacetonate; W catalysts such as $WCl_6$; Mo catalysts such as $MoCl_5$; Ta catalysts such as $TaCl_5$; Nb catalysts such as $NbCl_5$; Rh catalysts; and Pt catalysts.

In the invention, these metal catalysts may be used either singly or in combination.

In the invention, the metal catalyst is used in an amount of preferably from 0.001 to 2 moles, more preferably from 0.01 to 1 mole, especially preferably from 0.05 to 0.5 mole per mole of the monomer.

The polymerization reaction of the monomer of the invention is performed especially preferably in the presence of a radical polymerization initiator. For example, a monomer having a polymerizable carbon-carbon double bond or carbon-carbon triple bond can be polymerized in the presence of a polymerization initiator capable of exhibiting activity by generating a free radical such as carbon radical or oxygen radical upon heating.

As the radical polymerization initiator, organic peroxides and organic azo compounds are preferred, with organic peroxides being especially preferred.

Preferred examples of the organic peroxides include ketone peroxides such as "PERHEXA H", peroxyketals such as "PERHEXA TMH", hydroperoxides such as "PERBUTYL H-69", dialkylperoxides such as "PERCUMYL D", "PERBUTYL C" and "PERBUTYL D", diacyl peroxides such as "NYPER BW", peroxy esters such as "PERBUTYL Z" and "PERBUTYL L", and peroxy dicarbonates such as "PEROYL TCP", (each, trade name; commercially available from NOF Corporation), diisobutyryl peroxide, cumylperoxyneodecanoate, di-n-propylperoxydicarbonate, diisopropylperoxydicarbonate, di-sec-butylperoxydicarbonate, 1,1,3,3-tetramethylbutylperoxyneodecanoate, di(4-t-butylcyclohexyl)peroxydicarbonate, di(2-ethylhexyl)peroxydicarbonate, t-hexylperoxyneodecanoate, t-butylperoxyneodecanoate, t-butylperoxyneoheptanoate, t-hexylperoxypivalate, t-butylperoxypivalate, di(3,5,5-trimethylhexanoyl)peroxide, dilauroyl peroxide, 1,1,3,3-tetramethylbutylperoxy-2-ethylhexanoate, disuccinic acid peroxide, 2,5-dimethyl-2,5-di(2-ethylhexanoylperoxy)hexane, t-hexylperoxy-2-ethylhexanoate, di(4-methylbenzoyl) peroxide, t-butylperoxy-2-ethylhexanoate, di(3-methylbenzoyl) peroxide, benzoyl(3-methylbenzoyl)peroxide, dibenzoyl peroxide, 1,1-di(t-butylperoxy)-2-methylcyclohexane, 1,1-di(t-hexylperoxy)-3,3,5-trimethylcyclohexane, 1,1-di(t-hexylperoxy)cyclohexane, 1,1-di(t-butylperoxy)cyclohexane, 2,2-di(4,4-di-(t-butylperoxy)cyclohexyl)propane, t-hexylperoxyisopropyl monocarbonate, t-butylperoxymaleic acid, t-butylperoxy-3,5,5-trimethylhexanoate, t-butylperoxylaurate, t-butylperoxyisopropylmonocarbonate, t-butylperoxy-2-ethylhexylmonocarbonate, t-hexylperoxybenzoate, 2,5-dimethyl-2,5-di(benzoylperoxy) hexane, t-butylperoxyacetate, 2,2-di-(t-butylperoxy)butane, t-butylperoxybenzoate, n-butyl-4,4-di-t-butylperoxyvalerate, di(2-t-butylperoxyisopropyl)benzene, dicumyl peroxide, di-t-hexyl peroxide, 2,5-dimethyl-2,5-di(t-butylperoxy)hexane, t-butylcumyl peroxide, di-t-butyl peroxide, p-methane hydroperoxide, 2,5-dimethyl-2,5-di(t-butylperoxy)hexine-3, diisopropylbenzene hydroperoxide, 1,1,3,3-tetramethylbutyl hydroperoxide, cumene hydroperoxide, t-butyl hydroperoxide, 2,3-dimethyl-2,3-diphenylbutane, 2,4-dichlorobenzoyl peroxide, o-chlorobenzoyl peroxide, p-chlorobenzoyl peroxide, tris-(t-butylperoxy)triazine, 2,4,4-trimethylpentylperoxyneodecanoate, α-cumylperoxyneodecanoate, t-amylperoxy-2-ethylhexanoate, t-butylperoxyisobutyrate, di-t-butylperoxyhexahydroterephthalate, di-t-butylperoxytrimethyladipate, di-3-methoxybutylperoxydicarbonate, di-isopropylperoxydicarbonate, t-butylperoxyisopropylcarbonate, 1,6-bis(t-butylperoxycarbonyloxy)hexane, diethylene glycol bis(t-butylperoxycarbonate) and t-hexylperoxyneodecanoate.

Examples of the organic azo compound include azonitrile compounds such as "V-30", "V-40", "V-59", "V-60", "V-65" and "V-70", azoamide compounds such as "VA-080", "VA-085", "VA-086", "VF-096", "VAm-110" and "VAm-111", cyclic azoamidine compounds such as "VA-044" and "VA-061", and azoamidine compounds such as "V-50" and VA-057" (each, trade name; commercially available from Wako Pure Chemical Industries), 2,2-azobis(4-methoxy-2,4-dimethylvaleronitrile), 2,2-azobis(2,4-dimethylvaleronitrile), 2,2-azobis(2-methylpropionitrile), 2,2-azobis(2,4-dimethylbutyronitrile), 1,1-azobis(cyclohexane-1-carbonitrile), 1-[(1-cyano-1-methylethyl)azo]formamide, 2,2-azobis {2-methyl-N-[1,1-bis(hydroxymethyl)-2-hydroxyethyl]propionamide}, 2,2-azobis[2-methyl-N-(2-hydroxybutyl)propionamide], 2,2-azobis[N-(2-propenyl)-2-methylpropionamide], 2,2-azobis(N-butyl-2-methylpropionamide), 2,2-azobis(N-cyclohexyl-2-methylpropionamide), 2,2-azobis[2-(2-imidazolin-2-yl)propane]dihydrochloride, 2,2-azobis[2-(2-imidazolin-2-yl)]propane]disulfate dihydrate, 2,2-azobis{2-[1-(2-hydroxyethyl)-2-imidazolin-2-yl]propane}dihydrochloride, 2,2-azobis[2-[2-imidazolin-2-yl]propane], 2,2-azobis(1-imino-1-pyrrolidino-2-methylpropane)dihydrochloride, 2,2-azobis(2-methylpropionamidine)dihydrochloride, 2,2-azobis[N-(2-carboxyethyl)-2-methylpropionamidine] tetrahydrate, dimethyl-2,2-azobis(2-methylpropionate), 4,4-azobis(4-cyanovaleric acid) and 2,2-azobis(2,4,4-trimethylpentane).

These radical polymerization initiators to be used in the invention may be used either singly or in combination.

In the invention, the radical polymerization initiator is used in an amount of preferably from 0.001 to 2 moles, more preferably from 0.01 to 1 mole, especially preferably from 0.05 to 0.5 mole, per mole of the monomer.

Of these, organic peroxide radical polymerization initiators are especially preferred, because use of them enables preparation of a soluble polymer having high solubility in a coating solvent such as cyclohexanone in a high yield.

In the invention, the optimal conditions for the addition-polymerization reaction vary depending on the kind of the catalyst or solvent, the amount or concentration of the catalyst, or the like, but the inner temperature is preferably from 0 to 230° C., more preferably from 100 to 230° C., especially preferably from 140 to 200° C. and the reaction time is preferably from 1 to 50 hours, more preferably from 2 to 20 hours, especially preferably from 3 to 10 hours.

For preventing oxidative decomposition of the polymer, it is also preferred to perform the reaction in an inert gas atmosphere (for example, nitrogen or argon). The polymerization may be also preferably performed under light shielded conditions for suppressing an undesired photoreaction.

The weight (mass) average molecular weight of the polymer obtained by the polymerization is preferably from 1,000 to 500,000, more preferably from 3,000 to 300,000. When R=1, the weight average molecular weight is especially preferably from 5,000 to 180,000, still more preferably from 5,000 to 50,000. When R=0, it is especially preferably from 5,000 to 150,000, still more preferably from 5,000 to 60,000.

The polymer of the compound to be used in the invention is preferably a compound other than polyimide, that is, a compound having no polyimide bond from the standpoints of dielectric constant and absorption of a film.

The film forming composition preferred as a coating solution can be prepared by incorporating a coating solvent therein together with the polymer of the compound represented by the formula (I).

The polymer of the compound represented by formula (I) is preferably dissolved in a coating solvent at a sufficiently high concentration. As a target solubility, at 25° C., of the polymer in a coating solvent (for example, cyclohexanone) used for the manufacture of electronic devices is preferably 1 mass % or greater, more preferably 7 mass % or greater, especially preferably 10 mass % or greater.

Preferred examples of the coating solvent include alcohol solvents such as methanol, ethanol, isopropanol, 1-butanol, 2-ethoxymethanol and 3-methoxypropanol; ketone solvents such as acetone, acetylacetone, methyl ethyl ketone, methyl isobutyl ketone, 2-pentanone, 3-pentanone, 2-heptanone, 3-heptanone and cyclohexanone; ester solvents such as ethyl acetate, propyl acetate, butyl acetate, isobutyl acetate, pentyl acetate, ethyl propionate, propyl propionate, butyl propionate, isobutyl propionate, propylene glycol monomethyl ether acetate, methyl lactate, ethyl lactate and γ-butyrolactone; ether solvents such as diisopropyl ether, dibutyl ether, ethyl propyl ether, anisole, phenetole and veratrole; aromatic hydrocarbon solvents such as mesitylene, ethylbenzene, diethylbenzene, propylbenzene and 1,2-dichlorobenzene; and amide solvents such as N-methylpyrrolidinone and dimethylacetamide. These solvents may be used either singly or in combination.

Of these coating solvents, acetone, propanol, cyclohexanone, propylene glycol monomethyl ether acetate, methyl lactate, ethyl lactate, γ-butyrolactone, anisole, mesitylene and 1,2-dichlorobenzene are more preferred; cyclohexanone, propylene glycol monomethyl ether acetate, γ-butyrolactone and anisole are especially preferred.

The total solid concentration in the film forming composition is preferably from 1 to 50 mass %, more preferably from 2 to 20 mass %, especially preferably from 3 to 10 mass %.

The polymers of the invention may be used either singly or in combination.

The film forming composition of the invention may further contain an additive such as radical generator, nonionic surfactant, fluorine-containing nonionic surfactant, silane coupling agent and adhesion accelerator, within a range of not impairing the properties (such as heat resistance, dielectric constant, mechanical strength, coating properties, and adhesion) of the insulating film available using the composition.

Examples of the nonionic surfactant include octyl polyethylene oxide, decyl polyethylene oxide, dodecyl polyethylene oxide, octyl polypropylene oxide, decyl polypropylene oxide and dodecyl polypropylene oxide. Examples of the fluorine-containing nonionic surfactant include perfluorooctylpolyethylene oxide, perfluorodecylpolyethylene oxide and perfluorododecylpolyethylene oxide. Examples of the silane coupling agent include vinyltrimethoxysilane, vinyltriethoxysilane, vinyltriacetoxysilane, allyltrimethoxysilane, allyltriethoxysilane, divinyldiethoxysilane and trivinylethoxysilane.

These additives may each be added within a suitable range, depending on the using purpose of the additive or solid concentration of the coating solution. It is added usually in an amount of from 0.001 to 10%, more preferably from 0.01 to 5%, especially preferably from 0.05 to 2% in terms of mass % in the coating solution.

The film forming composition of the invention preferably contains a pore-forming agent. The pore-forming agent is a substance having a function of forming pores in a film obtained using the film forming composition. For example, a pore containing film can be obtained by heating a film, which has been formed using a film forming composition containing a pore-forming agent, to form pores in the film by the aid of the pore-forming agent.

Although no particular limitation is imposed on the pore-forming agent, a thermally decomposable polymer which decomposes by heat may be used. The polymer as the pore-forming agent is preferably a polymer which decomposes thermally at a temperature lower than the thermal decomposition temperature of the polymer constituting the film.

Examples of the thermally decomposable polymer usable as the pore-forming agent include polyvinyl aromatic compounds (such as polystyrene, polyvinylpyridine, halogenated polyvinyl aromatic compounds), polyacrylonitrile, polyalkylene oxides (such as polyethylene oxide and polypropylene oxide), polyethylene, polylactic acid, polysiloxane, polycaprolactone, polycaprolactam, polyurethane, polymethacrylates (such as polymethyl methacrylate), polymethacrylic acid, polyacrylates (such as polymethyl acrylate), polyacrylic acid, polydienes (such as polybutadiene and polyisoprene), polyvinyl chloride, polyacetal, and amine-capped alkylene oxides (commercially available under the trade name of Jeffamine™ Polyetheramine from Huntsman Corp.).

The polymer serving as the pore-forming agent may be any one of homopolymer, block copolymer, random copolymer or mixture thereof. Also, it may be a linear, branched, ultra-branched, dendritic or starlike polymer.

In particular, a polystyrene is preferably used as the pore-forming agent. Examples of the polystyrene include anionically polymerized polystyrene, syndiotactic polystyrene, and unsubstituted or substituted polystyrenes (such as poly(α-methylstyrene)), with unsubstituted polystyrenes being more preferred.

The pore-forming agent bound to a film forming compound is also preferred. The pore-forming agent with such a design enables formation of pores uniform in size, leading to reduction in the deterioration of mechanical strength.

The pore-forming agent may also be a granular substance having a size corresponding to the size of the pores produced in the insulating film. Such a substance has an average diameter of preferably 0.5 to 50 nm, more preferably from 0.5 to 20 nm. No limitation is imposed on the material of such a substance, and examples thereof include ultra-branched polymers such as dendrimer and latex particles, particularly crosslinked polystyrene-containing latexes.

Examples of such a substance include a polyamidamine (PAMAM) dendrimer available through Dendritech Inc. and described in Tomalia et al., *Polymer J.* (Tokyo), 17, 117 (1985); a polypropylenimine polyamine (DAB-Am) dendrimer available from DSM Corporation; a Frechet-type polyether dendrimer (described in Frechet et al., *J. Am. Chem.*

*Soc.*, 112, 7638(1990) and 113, 4252(1991)); a Percec-type liquid crystal monodendron, a dendronized polymer, and a self-aggregate polymer thereof (described in Percec et al., *Nature*, 391, 161(1998), *J. Am. Chem. Soc.*, 119, 1539(1997)); and a Boltorn H-series dendritic polyester (commercially available from Perstorp AB).

The suitable mass average molecular weight of the polymer as the pore-forming agent is preferably from 2,000 to 100,000, more preferably from 3,000 to 50,000, especially preferably from 5,000 to 20,000.

The pore-forming agent is added usually in an amount of preferably from 1 to 50 mass %, more preferably from 10 to 40 mass %, especially preferably from 20 to 30 mass %, based on the total solid content in the film forming composition.

The film forming composition of the invention preferably contains an adhesion accelerator.

Representative examples of the adhesion accelerator to be used in the invention include silanes, preferably organosilanes, for example, alkoxysilanes (such as trimethoxyvinylsilane, triethoxyvinylsilane, tetraethoxysilane, phenyltrimethoxysilane, allyltrimethoxysilane, and divinyldiethoxysilane) and acetoxysilanes (such as vinyltriacetoxysilane and 3-aminopropyltrimethoxysilane), and hydrolysates or dehydration condensates thereof; hexamethyldisilazane [(CH$_3$)$_3$—Si—NH—Si(CH$_3$)$_3$]; aminosilane couplers such as γ-aminopropyltriethoxysilane; and chelates (such as aluminum monoethylacetoacetate diisopropylate [(i-C$_3$H$_7$O)$_2$Al(OCOC$_2$H$_5$CHCOCH$_3$))] and aluminum alkoxide) from the standpoint of forming aluminum oxide. A mixture of these materials may also be usable. Commercially available adhesion accelerators may also be used.

The adhesion accelerator is added usually in an amount of from 0.05 to 5 mass %, preferably from 0.1 to 2 mass %, based on the total solid content in the film forming composition.

An insulating film can be formed by applying the coating solution of the invention on a substrate by an arbitrary method such as spin coating, roller coating, dip coating and scanning, and then removing the solvent by heat treatment. Heating for drying off the solvent may be performed in one stage or in two or more stages within a range of from 40 to 350° C. Heating is performed for 5 seconds to 300 seconds per stage. No particular limitation is imposed on the heating method, but a commonly employed method such as heating using a hot plate or furnace or light irradiation heating with a xenon lamp in RTP (rapid thermal processor) or the like may be applied.

The polymer of the invention is preferably cured by heat treatment after it is applied onto a substrate. For example, the polymer may be made insoluble and infusible by polymerizing, at the time of post heat-treatment, the carbon-carbon double bond or carbon-carbon triple bond which has remained in the polymer. This post-heat treatment is carried out preferably at from 100 to 450° C., more preferably from 200 to 420° C., especially preferably from 30 to 400° C., for preferably from 1 minute to 2 hours, more preferably from 10 minutes to 1.5 hours, especially preferably from 30 minutes to 1 hour.

The post-heat treatment may be performed in several times. This post-heat treatment is performed preferably in an inert gas atmosphere such as argon or nitrogen in order to prevent thermal oxidation by oxygen, with post-heat treatment in a nitrogen atmosphere being especially preferred.

The film obtained using the coating solution of the invention can be used for various purposes. For example, it is suited as an insulating film for electronic parts such as semiconductor device and multi-chip module multilayer wiring board. Specifically, it is usable as an interlayer insulating film, surface protective film or buffer coat film for semiconductors, a passivation film or α-ray shielding film in LSI, a coverlay film or overcoat film for flexographic plates, a cover coat or solder resist film for flexible copper-lined plates, a liquid crystal alignment film or the like.

In addition, the film of the invention is usable as a conductive film after doping the film with electron donors or acceptors to impart it with conductivity.

EXAMPLES

The invention will hereinafter be described by Examples, but the scope of the invention is not limited by or to them.

<Synthesis of Exemplified compound (D-2)>

In accordance with the process as described in a literature (*Tetrahedron Letters*, 42, 8645-8647(2001)), 3-bromo-1,1'-biadamantane (Compound A0) is prepared. Trisadamantane (Compound A1) is then synthesized by causing a coupling reaction between the compound A0 and 1-bromoadamantane in m-xyelene while adding thereto metal sodium. The compound A1 is brominated with bromine, followed by synthesis of a dibromotrisadamantane derivative (Compound A2). The compound A2 is reacted with vinyl bromide to yield a trisadamantane derivative (Compound A3) having two dibromoethyl groups. The compound A3 is reacted with t-butoxypotassium to obtain 1,3-bis(3-ethynyl-1-adamantyl)adamantane (Exemplified compound (D-2)).

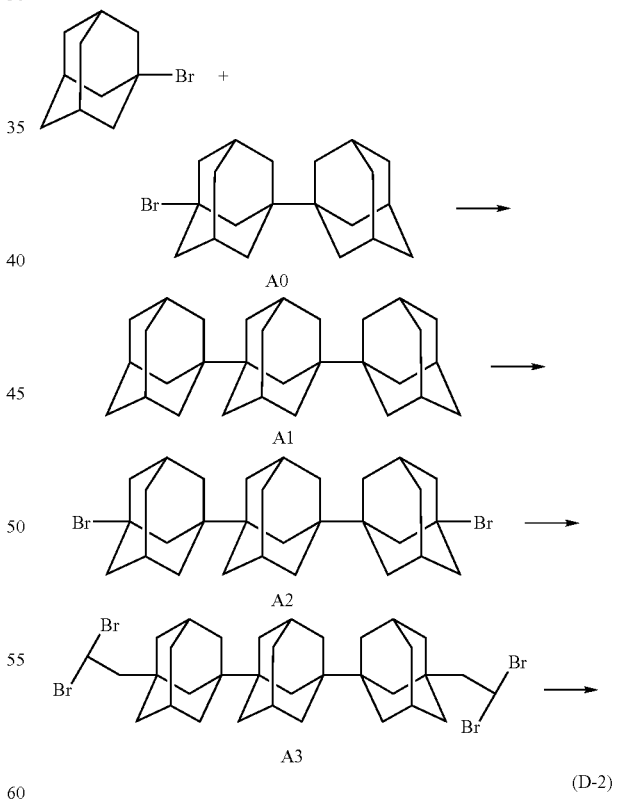

The elemental analysis values of Exemplified compound (D-2) thus obtained are as follows:

Elemental analysis for C$_{34}$H$_{44}$=452.71

Calculated: C, 90.20; H, 9.80; (%).

Found: C, 90.03; H, 9.62; (%).

Example 1

Under a nitrogen gas stream, 10 g of Exemplified compound (D-2), 50 ml of 1,3,5-triisopropylbenzene and 150 mg of Pd(PPh₃)₄ are stirred at an inner temperature of 200° C. for 10 hours. After the reaction mixture is cooled to room temperature and filtered to remove an insoluble matter, 300 ml of isopropyl alcohol is added to the filtrate. A solid thus precipitated is filtered and washed with isopropyl ether. As a result, 2.8 g of a polymer (A) having a weight average molecular weight of 150,000 is obtained. The solubility of the polymer (A) in cyclohexanone at 25° C. is 15 mass % or greater.

A coating solution is prepared by completely dissolving 1.0 of the polymer (A) in 7.3 g of cyclohexanone at room temperature. The resulting coating solution is filtered through a PTFE filter of 0.2 µm pore size, followed by spin coating onto a silicon wafer. The coating thus obtained is heated at 250° C. for 60 seconds on a hot plate under a nitrogen gas stream, and then baked for 60 minutes in an oven of 400° C. purged with nitrogen. As a result, a 0.5-µm thick uniform film with no particulates entrapped therein is obtained. The film is dipped in cyclohexanone for 5 hours at room temperature, but no decrease in film thickness occurs. The relative dielectric constant of the film is calculated from the capacitance at 1 MHz by using a mercury probe manufactured by Four Dimensions and "HP4285A LCR meter" (trade name; product of Yokogawa Hewlett Packard), resulting in 2.39. The film thus formed has good surface conditions. The dielectric constant of the film is measured at 25° C., which will equally apply hereinafter.

Example 2

In a similar manner to Example 1 except that anisole is used instead as the coating solvent, a film is formed. The film thus obtained has a dielectric constant of 2.39 and in addition, it has good surface conditions.

Example 3

Under a nitrogen gas stream, 2 g of Exemplified compound (D-2), 0.4 g of dicumyl peroxide ("Percumyl D", trade name; product of NOF) and 10 ml of t-butylbenzene are stirred for 4 hours at an inner temperature of 150° C., whereby polymerization is effected. The reaction mixture cooled to room temperature is added to 100 ml of methanol and a solid thus precipitated is filtered and washed with methanol. As a result, 1.5 g of a polymer (B) having a weight average molecular weight of about 12,000 is obtained.

The solubility of the polymer (B) in cyclohexanone is 15 mass % or greater at room temperature.

A coating solution is prepared by completely dissolving 1.0 g of the polymer (B) in 10 g of cyclohexanone at room temperature. The resulting coating solution is filtered completely through a PTFE filter of 0.1 µm pore size and spin-coated onto a silicon wafer. The coating is heated at 150° C. for 60 seconds on a hot plate under a nitrogen gas stream.

The coating is then baked for 60 minutes in an oven of 400° C. purged with nitrogen, whereby a 0.5 µm-thick uniform film having no particulates entrapped therein is obtained.

Dipping of the resulting film in cyclohexanone for 5 hours at room temperature does not cause any decrease in film thickness. The relative dielectric constant of the film is calculated from the capacitance at 1 MHz by using a mercury probe manufactured by Four Dimensions and "HP4285A LCR meter" (trade name; product of Yokogawa Hewlett Packard), resulting in 2.38. A Young's modulus (measured at 25° C.) of the film as measured by "Nanoindenter SA2" (trade name; product of MTS) is 8.0 MPa. In addition, the film has good surface conditions.

Example 4

In the following manner, 1,3-bis-(3-ethynyl-5,7-dimethyl-1-adamantyl)adamantane (Exemplified compound (D-32) is obtained. Described specifically, a coupling reaction between 1-bromoadamantane and 1-bromo-3,5-dimethyladamantane is caused in m-xylene by the addition of metal sodium, whereby 3,5-dimethyl-1,1'-biadamantane (Compound A4) is prepared. Compound A4 is then brominated with bromine into 3'-bromo-3,5-dimethyl-1,1'-biadamantane (Compound A5). Compound (A5) is reacted with 1-bromo-3,5-dimethyladamantane to obtain 1,3-bis-(3,5-dimethyl-1-adamantyl) adamantane (Compound A6). The resulting compound is then treated in a similar manner to that shown in <Synthesis of Exemplified compound (D-2)>, whereby Exemplified compound (D-32) is obtained.

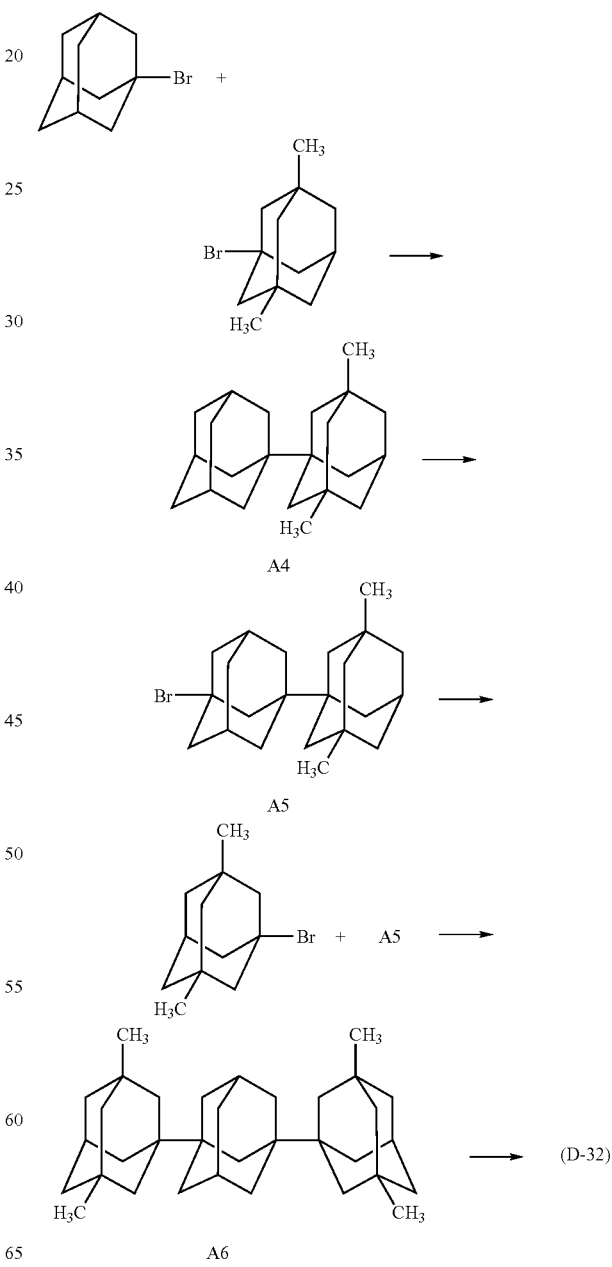

Under a nitrogen gas stream, 2 g of Exemplified compound (D-32), 0.4 g of dicumyl peroxide ("Percumyl D", trade name; product of NOF), and 10 ml of t-butylbenzene are stirred at an inner temperature of 150° C. for 5 hours, whereby polymerization is effected. The reaction mixture cooled to room temperature is added to 100 ml of methanol. A solid thus precipitated is filtered and washed with methanol. As a result, 1.4 g of a polymer (C) having a weight average molecular weight of 15,000 is obtained. A coating solution is prepared by completely dissolving 1.0 of the polymer (C) in 10 g of cyclohexanone at room temperature.

The resulting coating solution is filtered through a PTFE filter of 0.1 μm pore size, followed by spin coating onto a silicon wafer. The coating thus obtained is heated at 150° C. for 60 seconds on a hot plate under a nitrogen gas stream, and then baked for 60 minutes in an oven of 400° C. purged with nitrogen. As a result, a uniform 0.5-μm thick film having no particulates entrapped therein is obtained. The film is dipped in cyclohexanone at room temperature for 5 hours, but no decrease in film thickness occurs. The relative dielectric constant of the film is calculated from the capacitance at 1 MHz by using a mercury probe manufactured by Four Dimensions and "HP4285A LCR meter" (trade name; product of Yokogawa Hewlett Packard), resulting in 2.37. In addition, the film has good surface conditions.

Example 5

In accordance with the synthesis process of Exemplified compound (D-2), trisadamantane (Compound A1) is obtained. The trisadamantane thus obtained is brominated into 1-(3,5-dibromo-1-adamantyl)-3-(3-bromo-1-adamantyl)adamantane (Compound A7). The process thereafter is performed in accordance with the synthesis process of Exemplified compound D2, whereby 1-(3,5-diethynyl-1-adamantyl)-3-(3-ethynyl-1-adamantyl)adamantane (Exemplified compound (D-3)) is obtained.

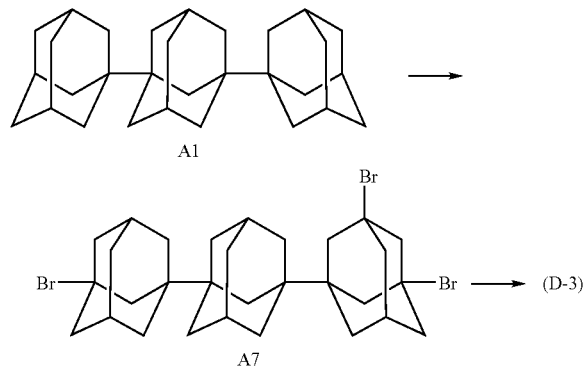

Under a nitrogen gas stream, 10 g of Exemplified compound (D-3), 50 ml of 1,3,5-triisopropylbenzene and 150 mg of Pd(PPh$_3$)$_4$ are stirred at an inner temperature of 200° C. for 10 hours. After the reaction mixture is cooled to room temperature and filtered to remove an insoluble matter, 300 ml of isopropyl alcohol is added to the filtrate. A solid thus precipitated is filtered and washed with isopropyl alcohol. As a result, 3.0 g of a polymer (D) having a weight average molecular weight of 100,000 is obtained. The solubility of the polymer (D) in cyclohexanone at room temperature is 15 mass % or greater.

A coating solution is prepared by completely dissolving 1.0 of the polymer (D) in 7.3 g of cyclohexanone at room temperature. The resulting coating solution is filtered through a PTFE filter of 0.2 μm pore size, followed by spin coating onto a silicon wafer. The coating is heated at 200° C. for 60 seconds on a hot plate under a nitrogen gas stream, and then baked in an oven of 400° C. purged with nitrogen. As a result, a 0.5-μm thick uniform film having no particulates entrapped therein is obtained. The film is dipped in cyclohexanone at room temperature for 5 hours, but no decrease in film thickness occurs. The relative dielectric constant of the film is calculated from the capacitance at 1 MHz by using a mercury probe manufactured by Four Dimensions and "HP4285A LCR meter" (trade name; product of Yokogawa Hewlett Packard), resulting in 2.37. In addition, the film has good surface conditions.

Example 6

In accordance with the synthesis process of Exemplified compound (D-2), trisadamantane (Compound A1) is obtained. The trisadamantane thus obtained is brominated into 1-bromotrisadamantane (Compound A8).

The resulting compound is thereafter treated also in accordance with the synthesis process of Exemplified compound (D-2) to obtain 1-ethynyltrisadamantane (Exemplified compound (D-1).

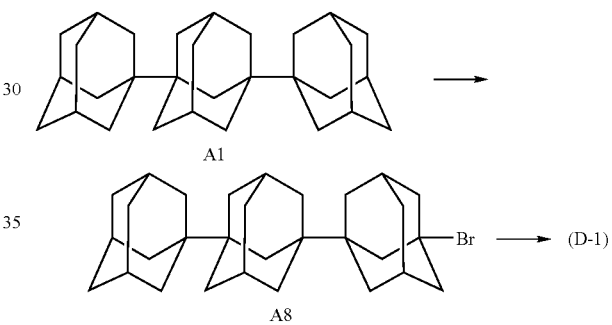

Under a nitrogen gas stream, 5 g of Exemplified compound (D-1), 5 g of Exemplified compound (D-2), 50 ml of 1,3,5-triisopropylbenzene and 150 mg of Pd(PPh$_3$)$_4$ are stirred at an inner temperature of 200° C. for 15 hours. After the reaction mixture is cooled to room temperature and filtered to remove an insoluble matter, 300 ml of isopropyl alcohol is added to the filtrate. A solid thus precipitated is filtered and washed with isopropyl alcohol. As a result, a 3.0 g of polymer (E) having a weight average molecular weight of 100,000 is obtained. The solubility of the polymer (E) in cyclohexanone at room temperature is 15 mass % or greater.

A coating solution is prepared by completely dissolving 1.0 of the polymer (E) in 7.3 g of cyclohexanone at room temperature. The resulting coating solution is filtered through a PTFE filter of 0.2 μm pore size, followed by spin coating onto a silicon wafer. The resulting coating is heated at 150° C. for 60 seconds on a hot plate under a nitrogen gas stream, and then baked for 60 minutes in an oven of 400° C. purged with nitrogen. As a result, a 0.5-μm thick uniform film having no particulates entrapped therein is obtained. The film is dipped in cyclohexanone at room temperature for 5 hours, but no decrease in film thickness occurs. The relative dielectric constant of the film is calculated from the capacitance at 1 MHz by using a mercury probe manufactured by Four Dimensions and "HP4285A LCR meter" (trade name; product of Yokogawa Hewlett Packard), resulting in 2.37. In addition, the film has good surface conditions.

Example 7

In a similar manner to Example 1, 8.3 g of a coating solution of the polymer (A) in cyclohexanone is prepared. Polystyrene (0.2 g) having a weight average molecular weight of 13,700 is added to the resulting solution as a pore-forming agent to completely dissolve the former in the latter. A coating is formed as in Example 1 by using the resulting coating solution. As a result, the film has a relative dielectric constant of 2.27 and has good surface conditions.

Example 8

In a similar manner to Example 5, 8.3 g of a coating solution in cyclohexanone of the polymer (D) is prepared. As a pore-forming agent, 0.2 g of polystyrene having a weight average molecular weight of 13,700 is added to the resulting coating solution to completely dissolve the former in the latter. To vinyltriacetoxysilane is added water in an amount of 3 times as much as that of vinyltriacetoxysilane, followed by stirring at room temperature for 10 minutes to cause hydrolysis and dehydration condensation, whereby a partial condensate is prepared as an adhesion accelerator. To the coating solution is added 10 mg of the resulting condensate to completely dissolve the latter in the former. A film is formed in a similar manner to Example 1 by using the coating solution thus obtained. The film thus obtained has a relative dielectric constant of 2.27 and in addition, has good surface conditions.

Comparative Example 1

After 5 g of 1,3,5-triethynyladamantane is reacted in 50 ml of anisole at 150° C. for 10 hours without using a catalyst, the reaction product is post treated in accordance with the process of Example 1, whereby 1.0 g of a polymer (F) is obtained. A coating solution is prepared by completely dissolving 1.0 g of the polymer (F) in 7.3 g of cyclohexanone at room temperature and a film is formed in a similar manner to Example 1. As a result of measurement, the film has a relative dielectric constant of 2.52 and in addition, it has bad surface conditions.

<Synthesis of Exemplified compound D-102>

In accordance with the process as described in a literature (*Journal of Polymer Science: Part A: Polymer Chemistry*, 30, 1747-1754(1992)), 3,3'-diethynyl-1,1'-biadamantane (DEBA) is obtained. In 20 ml of toluene is dissolved 15 g (41.7 mmol) of DEBA and 100 mL of DIBAL-H (1 M-hexane solution) is added to the resulting toluene solution while cooling the toluene solution. The resulting mixture is stirred at room temperature for 3 hours to yield a reaction mixture A'. In the next place, 200 mL of a saturated aqueous solution of ammonium chloride is cooled and the reaction mixture A' is added thereto. After filtration of the resulting mixture, the filtrate is extracted and organic components are distilled off, followed by drying, whereby 12 g (yield: 79%) of Exemplified compound (D-102) is obtained.

Elemental analysis values of Exemplified compound (D-102) thus obtained are as follows:

Elemental Analysis for $C_{24}H_{30}$=322.53
  Calculated: C 90.51, H 9.49 (%)
  Found: C 90.30, H 9.60 (%)

Example 9

Under a nitrogen gas stream, 5 g of Exemplified compound (D-102), 25 ml of 1,3,5-triisopropylbenzene and 75 mg of Pd(PPh$_3$)$_4$ are stirred at an inner temperature of 150° C. for 10 hours. After the reaction mixture is cooled to room temperature and filtered to remove an insoluble matter, 200 ml of isopropyl alcohol is added to the filtrate. A solid thus precipitated is filtered and washed with isopropyl alcohol. As a result, 1.5 g of a polymer (A') having a weight average molecular weight of 50,000 is obtained. The solubility of the polymer (A') in cyclohexanone at 25° C. is 15 mass % or greater.

A coating solution is prepared by completely dissolving 1.0 g of Polymer (A') in 7.3 g of cyclohexanone at room temperature. The resulting coating solution is filtered through a PTFE filter of 0.2 μm pore size, followed by spin coating onto a silicon wafer. The coating is heated at 250° C. for 60 seconds on a hot plate under a nitrogen gas stream, and then baked for 60 minutes in an oven of 400° C. purged with nitrogen. As a result, a 0.5-μm thick uniform film having no particulate entrapped therein is obtained. The film is dipped in cyclohexanone at room temperature for 5 hours, but no decrease in film thickness occurs. The relative dielectric constant of the film is calculated from the capacitance at 1 MHz by using a mercury probe manufactured by Four Dimensions and "HP4285A LCR meter" (trade name; product of Yokogawa Hewlett Packard), resulting in 2.40. In addition, the film has good surface conditions. The dielectric constant is measured at 25° C., which will equally apply hereinafter.

Example 10

In a similar manner to Example 9 except for the use of anisole instead as the coating solvent, a film is formed. The film has a dielectric constant of 2.40 and has good surface conditions.

Example 11

Under a nitrogen gas stream, 2 g of Exemplified compound (D-102), 0.4 g of dicumyl peroxide ("Percumyl D", trade name; product of NOF) and 10 ml of t-butylbenzene are stirred at an inner temperature of 150° C. for 5 hours, whereby polymerization is effected. The reaction mixture cooled to room temperature is added to 100 ml of methanol and a solid thus precipitated is filtered and washed with methanol. As a result, 1.5 g of a polymer (B') having a weight average molecular weight of about 14,000 is obtained.

A coating solution is prepared by completely dissolving 1.0 g of the polymer (B') in 10 g of cyclohexanone at room temperature. The resulting coating solution is filtered through a PTFE filter of 0.1 μm pore size, followed by spin-coating onto a silicon wafer. The coating is heated at 150° C. on a hot plate for 60 seconds under a nitrogen gas stream.

The coating is then baked for 60 minutes in an oven of 400° C. purged with nitrogen, whereby a 0.5 μm-thick uniform film having no particulates entrapped therein is obtained.

Dipping of the resulting film in cyclohexanone for 5 hours at room temperature does not cause any decrease in film thickness. The relative dielectric constant of the film is calculated from the capacitance at 1 MHz by using a mercury probe manufactured by Four Dimensions and "HP4285A LCR meter" (trade name; product of Yokogawa Hewlett Packard), resulting in 2.42. The film has a Young's modulus (measured at 25° C.) of 7.0 MPa when measured by "Nanoindenter SA2" (trade name; product of MTS) and in addition, it has good surface conditions.

Example 12

A coupling reaction of 1-bromo-3,5-dimethyladamantane (Compound A100, product of Aldrich) is caused in m-xylene by the addition of metal sodium, whereby 3,3',5,5'-tetramethyl-1,1'-biadamantane (Compound A101) is obtained. Compound A101 is then brominated with bromine into a dibromotetramethylbiadamantane derivative (Compound A102). Compound (A102) is reacted with vinyl bromide into Compound A103. The compound A103 is reacted with t-butoxypotassium to obtain 5,5',7,7'-tetramethyl-3,3'-diethynyl-1,1'-biadamantane (Compound A 104). Moreover, in accordance with the synthesis process shown in <Synthesis of Exemplified compound D-102>, a target Exemplified compound (D-134) (5,5',7,7'-tetramethyl-3,3'-divinyl-1,1'-biadamantane) is obtained.

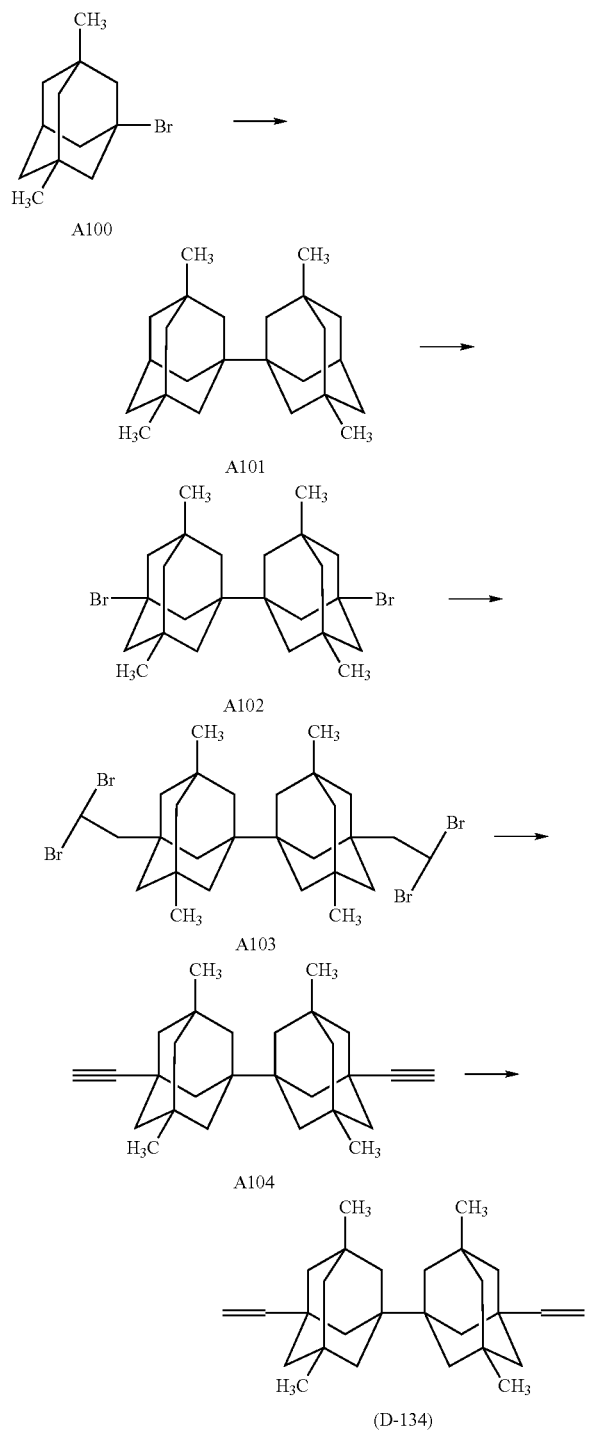

Under a nitrogen gas stream, 2 g of Exemplified compound (D-134), 0.4 g of dicumyl peroxide ("Percumyl D", trade name; product of NOF), and 10 ml of t-butylbenzene are stirred at an inner temperature of 150° C. for 6 hours, whereby polymerization is effected. The reaction mixture cooled to room temperature is added to 100 ml of methanol. A solid thus precipitated is filtered and washed with methanol. As a result, 1.3 g of a polymer (C') having a weight average molecular weight of 15,000 is obtained. A coating solution is prepared by completely dissolving 1.0 of the polymer (C') in 10 g of cyclohexanone at room temperature. The resulting coating solution is filtered through a PTFE filter of 0.1 μm pore size, followed by spin coating onto a silicon wafer. The coating thus formed is heated at 150° C. for 60 seconds on a hot plate under a nitrogen gas stream, and then baked for 60 minutes in an oven of 400° C. purged with nitrogen. As a result, a uniform 0.5-μm thick film having no particulates entrapped therein is obtained. The film is dipped in cyclohexanone at room temperature for 5 hours, but no decrease in film thickness occurs. The relative dielectric constant of the film is calculated from the capacitance at 1 MHz by using a mercury probe manufactured by Four Dimensions and "HP4285A LCR meter" (trade name; product of Yokogawa Hewlett Packard), resulting in 2.39. In addition, the film thus formed has good surface conditions.

Example 13

In accordance with the synthesis process of Example 12 by using 1-bromoadamantane (product of Aldrich), biadamantane is obtained. The biadamantane thus obtained is brominated into 3,3',5-tribromo-1,1'-biadamantane. The resulting product is treated in accordance with the synthesis process of Example 12, whereby Exemplified compound (D-103) (3,3'5-trivinyl-1,1'-biadamantane) is obtained as a target product.

Under a nitrogen gas stream, 10 g of Exemplified compound (D-103), 50 ml of 1,3,5-triisopropylbenzene and 150 mg of Pd(PPh$_3$)$_4$ are stirred at an inner temperature of 150° C. for 10 hours. After the reaction mixture is cooled to room temperature and filtered to remove an insoluble matter, 300 ml of isopropyl alcohol is added to the filtrate. A solid thus precipitated is filtered and washed with isopropyl alcohol. As a result, 2.9 g of a polymer (D') having a weight average molecular weight of 100,000 is obtained.

The solubility of the polymer (D') in cyclohexanone at room temperature is 15 mass % or greater.

A coating solution is prepared by completely dissolving 1.0 of Polymer (D') in 7.3 g of cyclohexanone at room temperature. The resulting coating solution is filtered through a PTFE filter of 0.2 μm pore size, followed by spin coating onto a silicon wafer. The coating thus formed is heated at 200° C. for 60 seconds on a hot plate under a nitrogen gas stream, and then baked for 60 seconds in an oven of 400° C. purged with nitrogen. As a result, a 0.5-μm thick uniform film having no particulates entrapped therein is obtained. The film is dipped in cyclohexanone at room temperature for 5 hours, but no decrease in film thickness occurs. The relative dielectric constant of the film is calculated from the capacitance at 1 MHz by using a mercury probe manufactured by Four Dimensions and "HP4285A LCR meter" (trade name; product of Yokogawa Hewlett Packard), resulting in 2.42. In addition, the film thus obtained has good surface conditions.

Example 14

Biadamantane is brominated into 3-bromo-1,1'-biadamantane. In accordance with the synthesis process shown in Example 12, Exemplified compound (D-101) (3-vinyl-1,1'-biadamantane) is obtained as a target product.

Under a nitrogen gas stream, 5 g of Exemplified compound (D-101), 5 g of Exemplified compound (D-102), 50 ml of 1,3,5-triisopropylbenzene and 150 mg of Pd(PPh$_3$)$_4$ are stirred at an inner temperature of 150° C. for 10 hours. After the reaction mixture is cooled to room temperature and filtered to remove an insoluble matter, 300 ml of isopropyl alcohol is added to the filtrate. A solid thus precipitated is filtered and washed with isopropyl alcohol. As a result, 3.0 g of a polymer (E') having a weight average molecular weight of 100,000 is obtained. The solubility of the polymer (E') in cyclohexanone at room temperature is 15 mass % or greater.

A coating solution is prepared by completely dissolving 1.0 of the polymer (E') in 7.3 g of cyclohexanone at room temperature. The resulting coating solution is filtered through a PTFE filter of 0.2 µm pore size, followed by spin coating onto a silicon wafer. The coating is heated at 150° C. for 60 seconds on a hot plate under a nitrogen gas stream, and then baked for 60 minutes in an oven of 400° C. purged with nitrogen. As a result, a 0.5-µm thick uniform film having no particulates entrapped therein is obtained. The film is dipped in cyclohexanone at room temperature for 5 hours, but no decrease in film thickness occurs. The relative dielectric constant of the film is calculated from the capacitance at 1 MHz by using a mercury probe manufactured by Four Dimensions and "HP4285A LCR meter" (trade name; product of Yokogawa Hewlett Packard), resulting in 2.40. In addition, the film thus obtained has good surface conditions.

Example 15

In a similar manner to Example 9, 8.3 g of a coating solution of the polymer (A') in cyclohexanone is prepared. As a pore-forming agent, 0.2 g of polystyrene having a weight average molecular weight of 13,700 is added to the resulting coating solution to completely dissolve the former in the latter. In a similar manner to Example 9, a film is formed using the resulting coating solution. The film thus obtained has a relative dielectric constant of 2.27. In addition, it has good surface conditions.

Example 16

In a similar manner to Example 13, 8.3 g of a coating solution of the polymer (D') in cyclohexanone is prepared. As a pore-forming agent, 0.2 g of polystyrene having a weight average molecular weight of 13,700 is added to the resulting solution to completely dissolve the former in the latter. To vinyltriacetoxysilane is added water in an amount of 3 times as much as that of vinyltriacetoxysilane, followed by stirring at room temperature for 10 minutes to cause hydrolysis and dehydration condensation, whereby a partial condensate is obtained as an adhesion accelerator. To the coating solution is added 10 mg of the resulting condensate to completely dissolve the latter in the former. A film is formed in a similar manner to Example 9 by using the coating solution thus obtained. The film has a relative dielectric constant of 2.3. In addition, it has good surface conditions.

Comparative Example 2

After 5 g of bisstyryladamantane represented by the below-described formula is reacted in 50 ml of anisole at 150° C. for 10 hours without using a catalyst, the reaction product is post treated in accordance with the process of Example 9, whereby 1.5 g of a polymer (F') is obtained. A coating solution is prepared by completely dissolving 1.0 g of the polymer (F') in 7.3 g of cyclohexanone at room temperature and a film is formed in a similar manner to Example 9. As a result of measurement, the film has a relative dielectric constant of 2.60. In addition it has bad surface conditions.

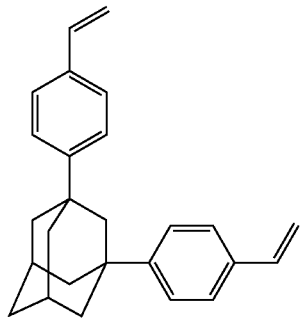

It has been understood that the films obtained in Examples using the film forming compositions of the invention are superior in relative dielectric constant and surface conditions compared with the films obtained in Comparative Examples.

The polymer available by polymerizing a compound of the invention has a sufficiently high solubility in a coating solvent, such as cyclohexanone, widely used in the electronic device production field; the film forming composition containing the polymer is uniform and is free from precipitation of an insoluble matter; and the insulating film formed using the composition has a low relative dielectric constant and a good surface condition and is usable as an interlayer insulating film in an electronic device or the like.

The entire disclosure of each and every foreign patent application from which the benefit of foreign priority has been claimed in the present application is incorporated herein by reference, as if fully set forth.

What is claimed is:

1. A film-forming composition comprising a polymer of a compound represented by formula (I):

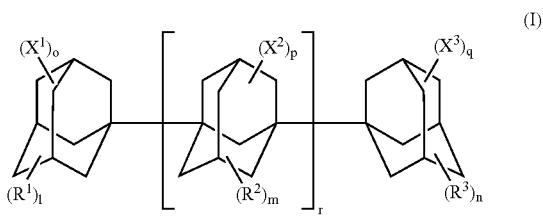

wherein R$^1$, R$^2$ and R$^3$ each independently represents an alkenyl group or an alkynyl group;

X$^1$, X$^2$ and X$^3$ each independently represents any substituent;

l and n each stands for an integer of from 0 to 15 and m stands for an integer of from 0 to 14, with the proviso that l, m and n do not represent 0 simultaneously;

o and q each independently stands for an integer of from 0 to 15 and p independently stands for an integer of from 0 to 14; and r stands for 0 or 1, with the proviso that when r=0, R$^1$ and R$^3$ each independently represents an alkenyl group.

2. The film-forming composition according to claim 1, wherein the polymer of the compound represented by formula (I) has a solubility of 1 mass % or greater in cyclohexanone at 25° C.

3. The film-forming composition according to claim 1, further comprising a coating solvent.

4. The film-forming composition according to claim 1, further comprising a pore-forming agent.

5. The film-forming composition according to claim 1, further comprising an adhesion accelerator.

6. An insulating film formed by use of the film-forming composition according to claim 1.

7. An electronic device comprising the insulating film according to claim 6.

8. A compound represented by formula (I):

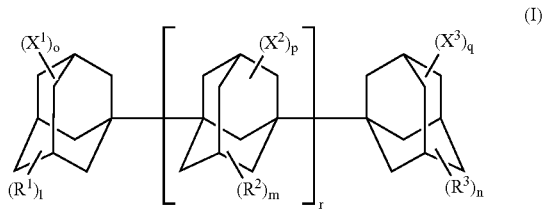

(I)

wherein $R^1$, $R^2$ and $R^3$ each independently represents an ethynyl group;

$X^1$, $X^2$ and $X^3$ each independently represents a hydrogen atom or a linear or branched $C_{1-10}$ alkyl group;

l and n each independently represents 0 or 1 with the proviso that l and n do not represent 0 simultaneously;

m represents 0, with the proviso that l, m and n do not represent 0 simultaneously;

o, p, and q each independently stands for an integer of from 0 to 2; and r represents 1.

9. A polymer obtained by polymerizing a compound represented by formula (I):

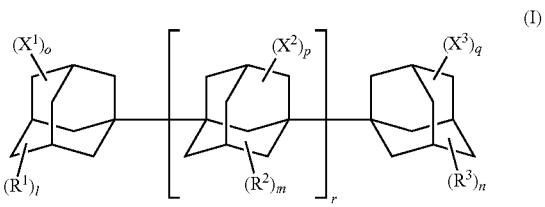

(I)

wherein $R^1$, $R^2$ and $R^3$ each independently represents an ethynyl group;

$X^1$, $X^2$ and $X^3$ each independently represents a hydrogen atom or a linear or branched $C_{1-10}$ alkyl group;

l and n each independently represents 0 or 1 with the proviso that l and n do not represent 0 simultaneously;

m represents 0, with the proviso that l, m and n do not represent 0 simultaneously;

o, p, and q each independently stands for an integer of from 0 to 2; and r represents 1.

10. The polymer of the compound represented by formula (I) according to claim 9, which is obtained by polymerizing the compound represented by formula (I) in the presence of a polymerization accelerator.

* * * * *